US007371819B2

(12) United States Patent
Escary

(10) Patent No.: US 7,371,819 B2
(45) Date of Patent: May 13, 2008

(54) POLYPEPTIDES OF THE IFNα-17 GENE

(75) Inventor: Jean-Louis Escary, Le Chesnay (FR)

(73) Assignee: GenOdyssee S.A., Evry (FR)

( * ) Notice: Subject to any disclaimer, the term of this patent is extended or adjusted under 35 U.S.C. 154(b) by 0 days.

(21) Appl. No.: 10/691,653

(22) Filed: Oct. 24, 2003

(65) Prior Publication Data
US 2004/0110715 A1 Jun. 10, 2004

Related U.S. Application Data

(63) Continuation of application No. PCT/EP02/05229, filed on Apr. 23, 2002.

(30) Foreign Application Priority Data
Apr. 24, 2001 (FR) .................................. 01 05516

(51) Int. Cl.
C07K 14/00 (2006.01)
A61K 38/21 (2006.01)
A61K 38/00 (2006.01)

(52) U.S. Cl. .......................... 530/350; 424/85.7; 514/2

(58) Field of Classification Search ...................... None
See application file for complete search history.

(56) References Cited

U.S. PATENT DOCUMENTS
6,299,877 B1 * 10/2001 Chen et al. ............... 424/158.1

FOREIGN PATENT DOCUMENTS
WO  WO 00/39280     7/2000
WO  WO 01/25438 A2  4/2001

OTHER PUBLICATIONS

Ngo et al., 1994, The Protein Folding Problem and Tertiary Structure Prediction, pp. 492-495.*
Wells, Aditivity of Mutational Effects in Protiens, 1990, Biochemistry, vol. 26, No. 37, pp. 8509-8517.*
International Search Report dated Jun. 13, 2003 for Application No. PCT/EP02/05229.
NCBI Sequence Viewer, Human gene for leukocyte (alpha) interferon C., ABSTRACT, 2 pages.
"DNA Sequence of Two Closely Linked Human Leukocyte Interferon Genes," Science, vol. 212, Jun. 5, 1981, pp. 1159-1162.
K. Henco[1,a], "Structural Relationship of Human Interferon Alpha Genes and Pseudogenes," J. Mol. Biol. (1995) vol. 185, pp. 227-260.
Axel Ullrich et al., "Nucleotide Sequence of a Portion of Human Chromosome 9 Containing a Leukocyte Interferon Gene Cluster," J. Mol. Biol. (1982) 156, pp. 467-486.
Ann-Christine Syvanen et al., "Identification of Individuals by Analysis of Biallelic DNA Markers, Ising PCR and Solid-Phase Minisequencing," AM. J. Genet., vol. 52, pp. 46-59, 1993.
H. Weber et al., "Single amino acid changes that render humna IFN-α2 biologically active on mouse cells," The EMBO Journal, vol. 6, No. 3, pp. 591-598, 1987.
Musaddeq Hussain et al., "Indentification of Interferon-α7, -α14, and -α21 Variants in the Genome of a Large Human Population," Journal of Interferon And Cytokine Research, vol. 16, pp. 853-859, (1996).
Rob L. H. Jansen et al., "Interleukin-2 and Interferon-α in the Treatment of Patients with Advanced Non-Small-Cell Lung Cancer," Journal Of Immunotherapy, vol. 12, No. 1, 1992, pp. 70-73.
Eiji Mita et al., "Predicting Interferon Therapy Efficacy from Hepatitis C Virus Genotype and RNA Titer," Digestive Diseases and Science, vol. 39, No. 5, (May 1994), pp. 977-982.
Ryo Yamada et al., "Identification of 142 single nucleotide polymorphisms in 41 candidate genes for rheumatoid arthritis in the Japanese population," Hum. Genet. (2000), vol. 106, pp. 293-297.
S. Cohen et al., "Cloning, Expression and Biological Activity of a New Variant of Human Interferon α Identified in Virus Induced Lymphoblastoid Cells," Develop. Biol. Standard., vol. 60, pp. 111-122, 1985.
O. I. Olopade et al., "Mapping of the Shortest Region of Overlap of Deletions of the Short Arm of Chromosome 9 Associated with Human Neoplasia," Genomics 14, pp. 437-443 (1992).

* cited by examiner

Primary Examiner—Christine J Saoud
Assistant Examiner—Jegatheesan Seharaseyon
(74) Attorney, Agent, or Firm—Hunton & Williams LLP

(57) ABSTRACT

The present invention relates to new polynucleotides derived from the nucleotide sequence of the IFNα-17 gene comprising new SNPs, and new polypeptides derived from the natural wild-type IFNα-17 protein comprising at least one mutation caused by at least one SNP of the invention, as well as their therapeutic uses.

16 Claims, 4 Drawing Sheets

POLYPEPTIDES OF THE IFNα-17 GENE

CROSS-REFERENCE TO RELATED APPLICATIONS

This application is a continuation of PCT Application No. PCT/EP02/05229, filed Apr. 23, 2002, which claims the benefit of French Patent Application No. 01/05516, filed Apr. 24, 2001.

BACKGROUND OF THE INVENTION

1. Field of the Invention

The present invention relates to new polynucleotides derived from the nucleotide sequence of the IFNα-17 gene comprising new SNPs, and new polypeptides derived from the natural wild-type IFNα-17 protein comprising mutations caused by these SNPs, as well as their therapeutic uses.

2. Related Art

The interferon alpha 17 gene, hereinafter referred to as IFNα-17, is described in the publications:

Olopade et al.: "Mapping of the shortest region of overlap of deletions of the short arm of chromosome 9 associated with human neoplasia"; Genomics; 14: 437-443; 1992.

Lawn R. M. et al.; "DNA sequence of two closely linked human leukocyte interferon genes"; Science 212 (4499), 1159-1162 (1981).

The nucleotide sequence of this gene is accessible under accession number V00532 in the GenBank database.

The IFNα are known for their cellular antiproliferative effects and their involvements in antiviral and antiparasitic responses.

The IFNα are also known to inhibit the expression of several other cytokines at the level of the hematopoietic stem cells, as well as to inhibit the cellular proliferation of certain tumors.

The IFNα are also known to reduce the expression of the receptors to the EGF in renal carcinomas, to inhibit the expression of certain mitochondrial genes, to inhibit the proliferation of fibroblasts, monocytes and B lymphocytes, especially in vitro, and to block the synthesis of antibodies by B lymphocytes.

The IFNα are also known to induce the expression of tumor specific antigens on the surface of tumor cells and also to induce the genes placed under the control of promoter regions of the ISRE type (Interferon-Stimulated Response Element) by acting on the specific transcription factors of these ISRE.

It is known that the IFNα are involved in different disorders and/or human diseases, such as the different cancers like for example, carcinomas, melanomas, lymphomas, leukemias and cancers of the liver, neck, head and kidneys, cardiovascular diseases, metabolic diseases such as those that are not connected with the immune system like, for example, obesity, infectious diseases such as hepatitis B and C and AIDS, pneumonias, ulcerative colitis, diseases of the central nervous system like, for example, Alzheimer's disease, schizophrenia and depression, the rejection of tissue or organ grafts, healing of wounds, anemia in dialyzed patients, allergies, asthma, multiple sclerosis, osteoporosis, psoriasis, rheumatoid arthritis, Crohn's disease, autoimmune diseases and disorders, gastrointestinal disorders or even disorders connected with chemotherapy treatments.

The IFNα are particularly used for the treatment of certain leukemias, metastasizing renal carcinomas as well as tumors that appear following an immunodeficiency, such as Kaposi's sarcoma in the case of AIDS. The IFNα are also effective against other types of tumors and against certain viral infections. The IFNα are also recognized by the FDA (Food and Drug Administration) for the treatment of genital warts or venereal diseases.

However, the IFNα, and in particular IFNα-17, have numerous side effects when they are used in pharmaceutical compositions, such as acute hypersensitivity (urticaria, bronchoconstriction, anaphylactic shock etc.), cardiac arrythmias, low blood pressure, epileptic seizures, problems with thyroid functions, flu-like syndromes (fevers, sweats, myalgias), etc.

Furthermore, the patients treated with IFNα can develop antibodies neutralizing these molecules, thus decreasing their effectiveness.

The inventor has found new polypeptide and new polynucleotide analogs to the IFNα-17 gene capable of having a different functionality from the natural wild-type IFNα-17 protein.

These new polypeptides and polynucleotides can notably be used to treat or prevent the disorders or diseases previously mentioned and avoid all or part of the disadvantages, which are tied to them.

BRIEF SUMMARY OF THE INVENTION

The invention has as its first object new polynucleotides that differ from the nucleotide sequence of the reference wild-type IFNα-17 gene, in that it comprises one or several SNPs (Single Nucleotide Polymorphism).

The nucleotide sequence SEQ ID NO. 1 of the human reference wild-type IFNα-17 gene is composed of 1873 nucleotides and comprises a coding sequence of 570 nucleotides, from nucleotide 639 (start codon) to the nucleotide 1208 (stop codon).

The applicant has identified 2 SNPs in the nucleotide sequence of the reference wild-type IFNα-17 gene.

These SNPs are the following: g771c, 808Ins(a).

It is understood, in the sense of the present invention, that the numbering corresponding to the positioning of the SNP previously defined is relative to the numbering of the nucleotide sequence SEQ ID NO. 1.

The letters a, t, c and g correspond respectively to the nitrogenous bases adenine, thymine, cytosine and guanine.

The first letter corresponds to the wild-type nucleotide, whereas the last letter corresponds to the mutated nucleotide.

Thus, the SNP g771c corresponds to a mutation of the nucleotide guanine (g) at position 771 of the nucleotide sequence SEQ ID NO. 1 of the reference wild-type IFNα-17 gene into a cytosine (c).

The SNP 808Ins(a) corresponds to the insertion of the nucleotide adenine (a) at position 808 of the nucleotide sequence SEQ ID NO. 1 of the reference wild-type IFNα-17 gene.

These SNPs were identified by the applicant using the determination process described in applicant's patent application FR 00 22894, entitled "Process for the determination of one or several functional polymorphism(s) in the nucleotide sequence of a preselected functional candidate gene and its applications" and filed Dec. 6, 2000, cited here by way of reference.

The process described in this patent application permits the identification of one (or several) preexisting SNP(s) in at least one individual from a random population of individuals.

In the scope of the present invention, a fragment of the nucleotide sequence of the IFNα-17 gene, comprising, for example, the coding sequence, was isolated from different individuals in a population of individuals chosen randomly.

Sequencing of these fragments was then carried out on certain of these samples having a heteroduplex profile (that is a profile different from that of the reference wild-type IFNα-17 gene sequence) after analysis by DHPLC ("Denaturing-High Performance Liquid Chromatography").

The fragment sequenced in this way was then compared to the nucleotide sequence of the fragment of the reference wild-type IFNα-17 gene and the SNPs in conformity with the invention identified.

Thus, the SNPs are natural and each of them is present in certain individuals of the world population.

The reference wild-type IFNα-17 gene codes for an immature protein of 189 amino acids, corresponding to the amino acid sequence SEQ ID NO. 2, that will be converted to a mature protein of 166 amino acids by cleavage of the signal peptide that includes the 23 first amino acids.

The coding SNPs of the invention, namely g771c and 808Ins(a), cause modifications at the level of the amino acid sequence of the protein encoded by the nucleotide sequence of the IFNα-17 gene. These modifications are the following:

The SNP g771c causes a mutation of the amino acid glycine (G) at position 45 in the immature protein of the IFNα-17 gene, corresponding to the amino acid sequence SEQ ID NO. 2, in arginine (R) and at position 22 of the mature protein. In the description of the present invention, one will indifferently call G22R and G45R the mutation encoded by this SNP according to whether one refers respectively to the mature protein or to the immature protein.

The SNP 808Ins(a) causes a mutation of the amino acid histidine (H) at position 57 in the immature protein of the IFNα-17 gene, corresponding to the amino acid sequence SEQ ID NO. 2, in glutamine (Q) and at position 34 of the mature protein. Moreover, the insertion of an adenine at position 808 on the nucleotide sequence causes a frameshift in the translation of the protein, which results in the appearance of a stop codon at position 58 of the amino acid sequence. Thus, the SNP 808Ins(a) causes a translation arrest just after the glutamine 57. As a consequence, the resulting immature protein is shortened and is only made of 57 amino acids. This polymorphism is also called H57Q frame 57. In the description of the present invention, one will indifferently call H34Q frame 34 and H57Q frame 57 the mutation encoded by this SNP according to whether one refers respectively to the mature protein or to the immature protein.

The amino acid sequence SEQ ID NO. 3 corresponds to the mutated immature protein (H57Q frame 57) encoded by the nucleotide sequence ID SEQ NO. 1 comprising the SNP 808Ins(a).

Each of the SNPs of the invention causes modifications of the spatial conformation of the polypeptides in conformity with the invention compared to the polypeptide encoded by the nucleotide sequence of the wild-type reference IFNα-17 gene.

These modifications can be observed by computational molecular modeling, according to methods that are well known to a person skilled in the art, making use of, for example, the modeling tools de novo (for example, SEQ-FOLD/MSI), homology (for example, MODELER/MSI), minimization of the force field (for example, DISCOVER, DELPHI/MSI) and/or molecular dynamics (for example, CFF/MSI).

One example of such models is given hereinafter in the experimental section.

Computational molecular modeling shows that the mutation G22R on the mutated mature protein involves a modification and a displacement of the AB loop around position 22, which causes the disappearance of hydrogene bonds.

FIGS. 1A and 1B show that the AB loop is unfolded and is protruding.

On the natural wild-type IFNα-17, the G22 residue is very near the R144 residue. This R144 residue is known to be involved in the binding of interferon α-2 (IFNα-2) to its receptor. The structure of IFNα-2 and of IFNα-17 being very similar, it is likely that the R144 residue in IFNα-17 is involved in the binding to its receptor.

Thus, the G22R mutated protein possesses a three-dimensional conformation different from the natural wild-type IFNα-17 protein.

Computational molecular modeling also permits the prediction that the presence of the amino acid arginine at position 22 involves a significant modification of the structure and of the function of the natural wild-type protein IFNα-17, notably at the level of the binding of IFNα-17 to its receptor.

Genotyping of the polynucleotides in conformity with the invention can be carried out in such a fashion as to determine the allelic frequency of these polynucleotides in a population.

The determination of the functionality of the polypeptides of the invention can equally be carried out by a test of their biological activity.

In this regard, it is possible to measure, for example, signal transduction, dendritic cell maturation, cytokine release by T-lymphocytes, cytokine release by monocytes, in vitro or in vivo antiviral activity, cellular antiproliferative activity on Daudi Burkitt's cell line, cellular antiproliferative activity on TF-1 cell line of polypeptides in conformity with the invention and compare with the wild-type IFNα-17, or the wild-type IFNα-2 chosen as representative of Intron A, a commercial product.

The invention also has for an object the use of polynucleotides and of polypeptides in conformity with the invention as well as of therapeutic molecules obtained and/or identified starting from these polynucleotides and polypeptides, notably for the prevention and the treatment of certain human disorders and/or diseases.

BRIEF DESCRIPTION OF THE DRAWINGS

In FIGS. 1A and 1B, the black ribbon represents the structure of the wild-type IFNα-17 protein and the white ribbon represents the structure of the G22R mutated IFNα-17 protein.

Figure 1:
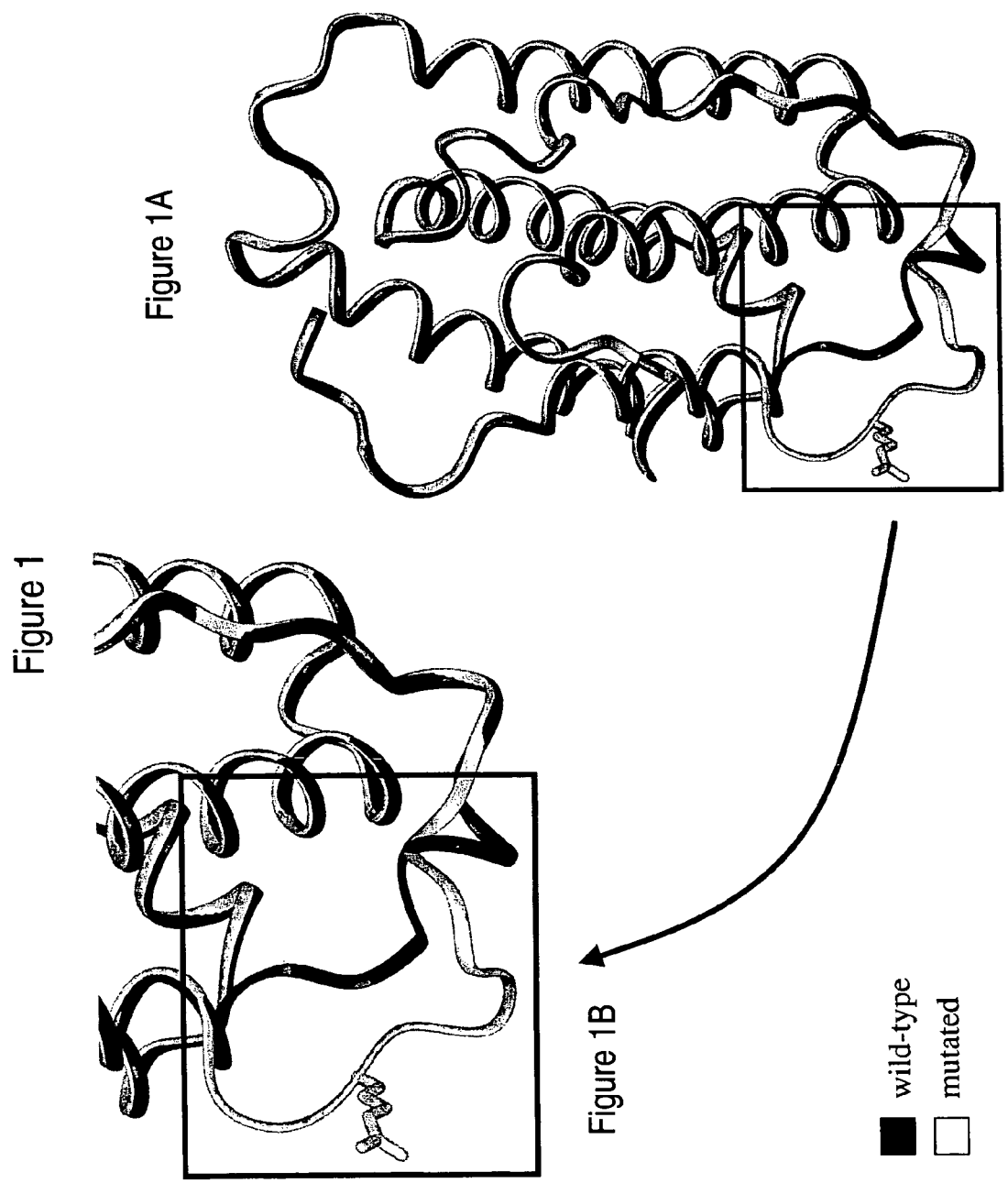
FIG. 1A represents a model of the encoded protein according to the invention comprising the SNP G45R and the wild-type IFNα-17 protein.
FIG. 1B represents a close up of the model of the inferior part of each one of the proteins represented in FIG. 1A.
Figure 2:
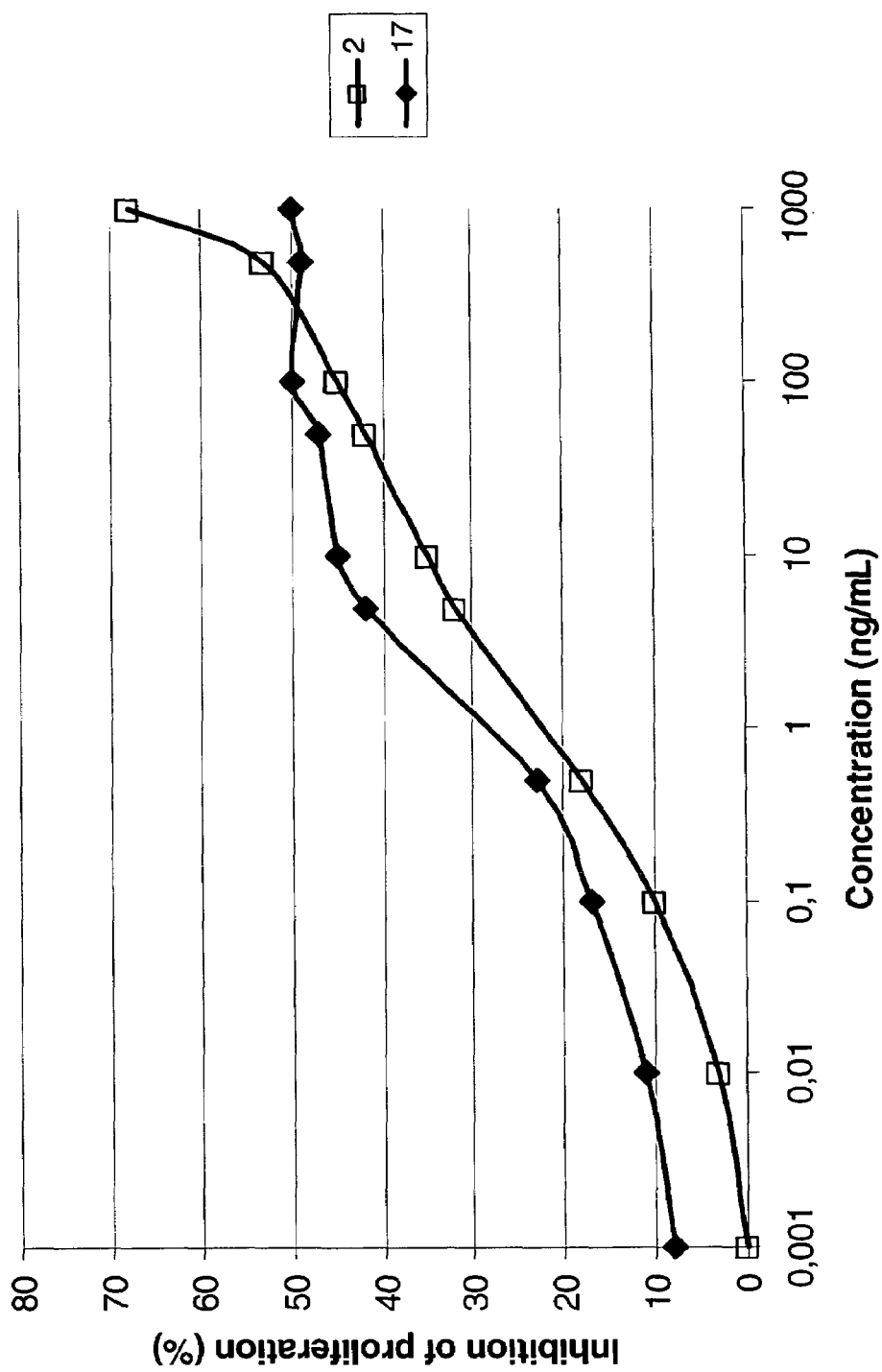
FIG. 2 represents the results of the test for measuring the antiproliferative effect of G45R mutated IFNα-17, on the TF-1 cell line. In this figure, the abscissas correspond to the concentration of IFNα (ng/mL) and the ordinates correspond to the inhibition of cell proliferation (%). The antiproliferative effect of the G45R mutated IFNα-17 (black diamonds) is compared to that of wild-type IFNα-2 (white squares).

In this figure, the abscissas correspond to the time of survival (days) and the ordinates correspond to the relative survival rate of VSV infected mice. The black diamonds represent the data for VSV infected mice treated with G45R mutated IFNα-17, the black squares represent the data for VSV infected mice treated with wild-type IFNα-2, and the open triangles represent the data for VSV infected mice that have not been treated.

DETAILED DESCRIPTION OF THE INVENTION

Definitions

"Nucleotide sequence of the reference wild-type gene" is understood as the nucleotide sequence SEQ ID NO. 1 of the human IFNα-17 gene.

This sequence is accessible in GenBank under Accession number V00532 and described in:

- Olopade et al.: "Mapping of the shortest region of overlap of deletions of the short arm of chromosome 9 associated with human neoplasia"; Genomics; 14: 437-443; 1992.
- Lawn R. M. et al.; "DNA sequence of two closely linked human leukocyte interferon genes"; Science 212 (4499), 1159-1162 (1981).
- "Natural wild-type IFNα-17 protein" or "wild-type IFNα-17 protein" are understood as the mature protein encoded by the nucleotide sequence of the reference wild-type IFNα-17 gene. The natural wild-type immature protein IFNα-17 corresponds to the peptide sequence shown in SEQ ID NO. 2.

"Polynucleotide" is understood as a polyribonucleotide or a polydeoxyribonucleotide that can be a modified or non-modified DNA or an RNA.

The term polynucleotide includes, for example, a single strand or double strand DNA, a DNA composed of a mixture of one or several single strand region(s) and of one or several double strand region(s), a single strand or double strand RNA and an RNA composed of a mixture of one or several single strand region(s) and of one or several double strand region(s). The term polynucleotide can also include an RNA and/or a DNA including one or several triple strand regions. By polynucleotide is equally understood the DNAs and RNAs containing one or several bases modified in such a fashion as to have a skeleton modified for reasons of stability or for other reasons. By modified base is understood, for example, the unusual bases such as inosine.

"Polypeptide" is understood as a peptide, an oligopeptide, an oligomer or a protein comprising at least two amino acids joined to each other by a normal or modified peptide bond, such as in the cases of the isosteric peptides, for example.

A polypeptide can be composed of amino acids other than the 20 amino acids defined by the genetic code. A polypeptide can equally be composed of amino acids modified by natural processes, such as post translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends.

A polypeptide can be branched following an ubiquitination or be cyclic with or without branching. This type of modification can be the result of natural or synthetic post-translational processes that are well known to a person skilled in the art.

For example, polypeptide modifications is understood to include acetylation, acylation, ADP-ribosylation, amidation, covalent fixation of flavine, covalent fixation of heme, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, cysteine formation, pyroglutamate formation, formylation, gamma-carboxylation, glycosylation, GPI anchor formation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature: PROTEINS-STRUCTURE AND MOLECULAR PROPERTIES, 2nd Ed.; T. E. Creighton, New York, 1993, POST-TRANSLATIONAL COVALENT MODIFICATION OF PROTEINS, B. C. Johnson, Ed., Academic Press, New York, 1983, Seifter et al. "Analysis for protein modifications and nonprotein cofactors", Meth. Enzymol. (1990) 182: 626-646, and Rattan et al. "Protein Synthesis: Post-translational Modifications and Aging", Ann NY Acad Sci (1992) 663: 48-62.

"Isolated polynucleotide" or "isolated polypeptide" are understood as a polynucleotide or a polypeptide respectively such as previously defined which is isolated from the human body or otherwise produced by a technical process.

"Identity" is understood as the measurement of nucleotide or polypeptide sequence identity.

Identity is a term well known to a person skilled in the art and well described in the literature. See COMPUTATIONAL MOLECULAR BIOLOGY, Lesk, A. M., Ed., Oxford University Press, New York, 1998; BIOCOMPUTING INFORMATICS AND GENOME PROJECT, Smith, D. W., Ed., Academic Press, New York, 1993; COMPUTER ANALYSIS OF SEQUENCE DATA, PART I, Griffin, A. M. and Griffin H. G., Ed, Humana Press, New Jersey, 1994; and SEQUENCE ANALYSIS IN MOLECULAR BIOLOGY, von Heinje, G., Academic Press, 1987.

The methods commonly employed to determine the identity and the similarity between two sequences are equally well described in the literature. See GUIDE TO HUGE COMPUTER, Martin J. Bishop, Ed, Academic Press, San Diego, 1994, and Carillo H. and Lipton D., Siam J Applied Math (1988) 48: 1073.

A polynucleotide having, for example, an identity of at least 95% with the nucleotide sequence SEQ ID NO. 1 is a polynucleotide which contains at most 5 points of mutation over 100 nucleotides, compared to said sequence.

These points of mutation can be one or more substitution(s), addition(s) and/or deletion(s) of one or more nucleotide(s).

In the same way, a polypeptide having, for example, an identity of at least 95% with the amino acid sequence SEQ ID NO. 2 is a polypeptide that contains at most 5 points of mutation over 100 amino acids, compared to said sequence.

These points of mutation can be one (or several) substitution(s), addition(s) and/or deletion(s) of one (or several) amino acid(s).

The polynucleotides and the polypeptides according to the invention which are not totally identical with, respectively:
  the nucleotide sequence SEQ ID NO. 1 comprising at least one of the following SNPs: g771c and 808Ins(a)
  the amino acid sequence SEQ ID NO. 2 comprising the SNP G45R
  the amino acid sequence SEQ ID NO. 3 possibly comprising the SNP G45R,
are considered as variants of these sequences.

Usually a polynucleotide according to the invention possesses the same or practically the same biological activity as the nucleotide sequence SEQ ID NO. 1 comprising at least one of the SNPs: g771c and 808Ins(a).

In similar fashion, usually a polypeptide according to the invention possesses the same or practically the same biological activity as:
  the amino acid sequence SEQ ID NO. 2 comprising the SNP G45R, and/or
  the amino acid sequence SEQ ID NO. 3 possibly comprising the SNP G45R.

A variant, according to the invention, can be obtained, for example, by site-directed mutagenesis or by direct synthesis.

By "SNP" is understood any natural variation of a base in a nucleotide sequence. A SNP, on a nucleotide sequence, can be coding, silent or non-coding.

A coding SNP is a polymorphism included in the coding sequence of a nucleotide sequence that involves a modification of an amino acid in the sequence of amino acids encoded by this nucleotide sequence. In this case, the term SNP applies equally, by extension, to a mutation in an amino acid sequence.

A silent SNP is a polymorphism included in the coding sequence of a nucleotide sequence that does not involve a modification of an amino acid in the amino acid sequence encoded by this nucleotide sequence.

A non-coding SNP is a polymorphism included in the non-coding sequence of a nucleotide sequence. This polymorphism can notably be found in an intron, a splicing zone, a transcription promoter or a site enhancer sequence.

By "functional SNP" is understood a SNP, such as previously defined, which is included in a nucleotide sequence or an amino acid sequence, having a functionality.

By "functionality" is understood the biological activity of a polypeptide or of a polynucleotide.

The functionality of a polypeptide or of a polynucleotide according to the invention can consist in a conservation, an augmentation, a reduction or a suppression of the biological activity of the polypeptide encoded by the nucleotide sequence of the wild-type reference gene or of this latter nucleotide sequence.

The functionality of a polypeptide or of a polynucleotide according to the invention can equally consist in a change in the nature of the biological activity of the polypeptide encoded by the nucleotide sequence of the reference wild-type gene or of this latter nucleotide sequence.

The biological activity can, notably, be linked to the affinity or to the absence of affinity of a polypeptide according to the invention with a receptor.

Polynucleotide

The present invention has for its first object an isolated polynucleotide comprising:
  a) a nucleotide sequence having at least 90% identity, preferably at least 95% identity, and more preferably at least 99% identity with the sequence SEQ ID NO. 1 or its coding sequence (of the nucleotide 639 to the nucleotide 1208),
  it being understood that this nucleotide sequence comprises at least one of the following coding SNPs: g771c and 808Ins(a), or
  b) a nucleotide sequence complementary to a nucleotide sequence under a).

In conformity with the present invention, the nucleotide sequence under a) may comprise the SNP g771c, or the SNP 808Ins(a), or both SNPs g771c and 808Ins(a).

It is understood, in the sense of the present invention, that the numbering corresponds to the positioning of the SNPs in the nucleotide sequence SEQ ID NO. 1.

The present invention relates equally to an isolated polynucleotide comprising:
  a) a nucleotide sequence SEQ ID NO. 1 or its coding sequence, it being understood that each of these sequences comprises at least one of the following coding SNPs: g771c and 808Ins(a), or
  b) a nucleotide sequence complementary to a nucleotide sequence under a).

Preferably, the polynucleotide of the invention consists of the sequence SEQ ID NO. 1 or its coding sequence, it being understood that each of these sequences comprises at least one of the following coding SNPs: g771c and 808Ins(a).

According to the invention, the polynucleotide previously defined comprises a single coding SNP selected from the group consisting of: g771c and 808Ins(a).

The present invention also concerns an isolated polynucleotide consisting of a part of:
  a) a nucleotide sequence SEQ ID NO. 1 or its coding sequence, it being understood that each of these sequences comprises at least one of the following SNPs: g771c and 808Ins(a), or
  b) a nucleotide sequence complementary to a nucleotide sequence under a).
said isolated polynucleotide being composed of at least 10 nucleotides.

Preferably, the isolated polynucleotide as defined above is composed of 10 to 40 nucleotides.

The present invention also has for its object an isolated polynucleotide coding for a polypeptide comprising:
  a) the amino acid sequence SEQ ID NO. 2, or
  b) the amino acid sequence comprising the amino acids included between positions 24 and 189 of the sequence of amino acids SEQ ID NO. 2,
  it being understood that each of the amino acid sequences under a) and b) comprises the following coding SNP: G45R.

It is understood, in the sense of the present invention, that the numbering corresponding to the positioning of the SNP G45R is relative to the numbering of the amino acid sequence SEQ ID NO. 2.

The present invention also has for its object an isolated polynucleotide coding for a polypeptide comprising:
  a) the amino acid sequence SEQ ID NO. 3, or
  b) the amino acid sequence comprising the amino acids included between positions 24 and 57 of the sequence of amino acids SEQ ID NO. 3, Each of the amino acid sequences under a) and b) of the previously defined polypeptide may also comprise the SNP G45R.

According to a preferred object of the invention, the previously defined polypeptide comprises a single coding SNP such as defined above.

More preferably, an isolated polynucleotide according to the invention codes for a polypeptide comprising all or part of the amino acid sequence SEQ ID NO. 2 and having the coding SNP G45R.

More preferably, an isolated polynucleotide according to the invention codes for a polypeptide comprising all or part of the amino acid sequence SEQ ID NO. 3, possibly also having the coding SNP G45R.

Preferably a polynucleotide according to the invention is composed of a DNA or RNA molecule.

A polynucleotide according to the invention can be obtained by standard DNA or RNA synthetic methods.

A polynucleotide according to the invention comprising SNP g771c can equally be obtained by site-directed mutagenesis starting from the nucleotide sequence of the IFNα-17 gene and modifying the wild-type nucleotide guanine (g) to the mutated nucleotide cytosine (c) at position 771 of the nucleotide sequence SEQ ID NO. 1.

A polynucleotide according to the invention comprising SNP 808Ins(a) can equally be obtained by site-directed mutagenesis starting from the nucleotide sequence of the IFNα-17 gene by adding an adenine nucleotide (a) at position 808 of the nucleotide sequence SEQ ID NO. 1.

The processes of site-directed mutagenesis that can be implemented in this way are well known to a person skilled in the art. The publication of T A Kunkel in 1985 in "Proc. Natl. Acad. Sci. USA" 82:488 can notably be mentioned.

An isolated polynucleotide can equally include, for example, nucleotide sequences coding for pre-, pro- or pre-pro-protein amino acid sequences or marker amino acid sequences, such as hexa-histidine peptide.

A polynucleotide of the invention can equally be associated with nucleotide sequences coding for other proteins or protein fragments in order to obtain fusion proteins or other purification products.

A polynucleotide according to the invention can equally include nucleotide sequences such as the 5' and/or 3' non-coding sequences, such as, for example, transcribed or non-transcribed sequences, translated or non-translated sequences, splicing signal sequences, polyadenylated sequences, ribosome binding sequences or even sequences which stabilize mRNA.

A nucleotide sequence complementary to the nucleotide or polynucleotide sequence is defined as one that can hybridize with this nucleotide sequence, under stringent conditions.

"Stringent hybridization conditions" is generally but not necessarily understood as the chemical conditions that permit a hybridization when the nucleotide sequences have an identity of at least 80%, preferably greater than or equal to 90%, still more preferably greater than or equal to 95% and most preferably greater than or equal to 97%.

The stringent conditions can be obtained according to methods well known to a person skilled in the art and, for example, by an incubation of the polynucleotides, at 42° C., in a solution comprising 50% formamide, 5×SSC (150 mM of NaCl, 15 mM of trisodium citrate), 50 mM of sodium phosphate (pH=7.6), 5× Denhardt Solution, 10% dextran sulfate and 20 μg denatured salmon sperm DNA, followed by washing the filters at 0.1×SSC, at 65° C.

Within the scope of the invention, when the stringent hybridization conditions permit hybridization of the nucleotide sequences having an identity equal to 100%, the nucleotide sequence is considered to be strictly complementary to the nucleotide sequence such as described under a).

It is understood within the meaning of the present invention that the nucleotide sequence complementary to a nucleotide sequence comprises at least one anti-sense SNP according to the invention.

Thus, for example, if the nucleotide sequence comprises the SNP g771c, its complementary nucleotide sequence comprises the nucleotide g at the equivalent of position 771.

Identification, Hybridization and/or Amplification of a Polynucleotide Comprising a SNP The present invention also has for its object the use of all or part of:

a) a polynucleotide having 80 to 100% identity (preferably at least 90% identity, more preferably 95% identity and particularly 100% identity) with the nucleotide sequence SEQ ID NO. 1, and/or b) a polynucleotide according to the invention comprising at least one SNP in order to identify, hybridize and/or amplify all or part of a polynucleotide having 80 to 100% identity (preferably at least 90% identity, more preferably 95% identity and particularly 100% identity) with the nucleotide sequence SEQ ID NO. 1 or if necessary its coding sequence (from nucleotide 639 to nucleotide 1208), it being understood that each one of these sequences comprises at least one of the following SNPs: g771c, 808Ins(a).

Genotyping and Determination of the Frequency of a SNP

The present invention equally has for its object the use of all or part of:

a) a polynucleotide having 80 to 100% identity (preferably at least 90% identity, more preferably 95% identity and particularly 100% identity) with the nucleotide sequence SEQ ID NO. 1, and/or b) a polynucleotide according to the invention comprising at least one SNP for the genotyping of all or part of a polynucleotide having 80 to 100% identity (preferably at least 90% identity, more preferably 95% identity and particularly 100% identity) with the nucleotide sequence SEQ ID NO. 1 or if necessary its coding sequence (from nucleotide 639 to nucleotide 1208), it being understood that each one of these sequences comprises at least one of the following SNPs: g771c, 808Ins(a).

According to the invention, the genotyping may be carried out on an individual or a population of individuals.

Within the meaning of the invention, genotyping is defined as a process for the determination of the genotype of an individual or of a population of individuals. Genotype consists of the alleles present at one or more specific loci.

"Population of individuals" is understood as a group of individuals selected in random or non-random fashion. These individuals can be humans, animals, microorganisms or plants.

Usually, the group of individuals comprises at least 10 individuals, preferably from 100 to 300 individuals.

The individuals can be selected according to their ethnicity or according to their phenotype, notably those who are affected by the following disorders and/or diseases: carcinomas, melanomas, lymphomas, leukemias and cancers of the liver, neck, head and kidneys, cardiovascular diseases, metabolic diseases such as those that are not connected with the immune system like, for example, obesity, infectious diseases in particular viral infections like hepatitis B and C and AIDS, pneumonias, ulcerative colitis, diseases of the central nervous system like, for example, Alzheimer's disease, schizophrenia and depression, the rejection of tissue or organ grafts, healing of wounds, anemia in dialyzed patients, allergies, asthma, multiple sclerosis, osteoporosis, psoriasis, rheumatoid arthritis, Crohn's disease, autoimmune diseases and disorders, gastrointestinal disorders or even disorders connected with chemotherapy treatments.

A functional SNP according to the invention is preferably genotyped in a population of individuals.

Multiple technologies exist which can be implemented in order to genotype SNPs (see notably Kwok Pharmacogenomics, 2000, vol 1, pp 95-100. "High-throughput genotyping assay approaches"). These technologies are based on one of the four following principles: allele specific oligonucleotide hybridization, oligonucleotide elongation by dideoxynucleotides optionally in the presence of deoxynucleotides, ligation of allele specific oligonucleotides or cleavage of allele specific oligonucleotides. Each one of these technologies can be coupled to a detection system such as measurement of direct or polarized fluorescence, or mass spectrometry.

Genotyping can notably be carried out by minisequencing with hot ddNTPs (2 different ddNTPs labeled by different fluorophores) and cold ddNTPs (2 different non labeled ddNTPs), in connection with a polarized fluorescence scanner. The minisequencing protocol with reading of polarized fluorescence (FP-TDI Technology or Fluorescence Polarization Template-direct Dye-Terminator Incorporation) is well known to a person skilled in the art.

It can be carried out on a product obtained after amplification by polymerase chain reaction (PCR) of the DNA of each individual. This PCR product is selected to cover the polynucleotide genic region containing the studied SNP. After the last step in the PCR thermocycler, the plate is placed on a polarized fluorescence scanner for a reading of the labeled bases by using fluorophore specific excitation and emission filters. The intensity values of the labeled bases are reported on a graph.

For the PCR amplification, in the case of one SNP of the invention, the sense and antisense primers, respectively, can easily be selected by a person skilled in the art according to the position of the SNPs of the invention.

For example, the sense and antisense nucleotide sequences for the PCR amplification primers can be, respectively:

SEQ ID NO. 4: Sense primer: TTCAAGGTTAC-CCATCTCAA

SEQ ID NO. 5: Antisense primer: TTAGTCAATCAG-GATCATTGC

The nucleotide sequences permit amplification of a fragment having a length of 655 nucleotides, from nucleotide 591 to nucleotide 1245 in the nucleotide sequence SEQ ID NO. 1.

A statistical analysis of the frequency of each allele (allelic frequency) encoded by the gene comprising the SNP in the population of individuals is then achieved, which permits determination of the importance of their impact and their distribution in the different sub-groups and notably, if necessary, the diverse ethnic groups that constitute this population of individuals.

The genotyping data are analyzed in order to estimate the distribution frequency of the different alleles observed in the studied populations. The calculations of the allelic frequencies can be carried out with the help of software such as SAS-suite® (SAS) or SPLUS® (MathSoft). The comparison of the allelic distributions of a SNP of the invention across different ethnic groups of the population of individuals can be carried out by means of the software ARLEQUIN® and SAS-suite®.

SNPs of the Invention as Genetic Markers

Whereas SNPs modifying functional sequences of genes (e.g. promoter, splicing sites, coding region) are likely to be directly related to disease susceptibility or resistance, all SNPs (functional or not) may provide valuable markers for the identification of one or several genes involved in these disease states and, consequently, may be indirectly related to these disease states (See Cargill et al. (1999). Nature Genetics 22:231-238; Riley et al. (2000). Pharmacogenomics 1:39-47; Roberts L. (2000). Science 287: 1898-1899).

Thus, the present invention also concerns a databank comprising at least one of the following SNPs: g771c, 808Ins(a), in a polynucleotide of the IFNα-17 gene.

It is well understood that said SNPs are numbered in accordance with the nucleotide sequence SEQ ID NO. 1.

This databank may be analyzed for determining statistically relevant associations between:

(i) at least one of the following SNPs: g771c, 808Ins(a), in a polynucleotide of the IFNα-17 gene, and (ii) a disease or a resistance to a disease.

More preferably, the present invention concerns a method for determining statistically relevant associations between at least one SNP selected from the group consisting of g771c, 808Ins(a), in the IFNα-17 gene, and a disease or resistance to disease comprising:

Genotyping a group of individuals;

Determining the distribution of said disease or resistance to disease within said group of individuals;

Comparing the genotype data with the distribution of said disease or resistance to disease; and Analyzing said comparison for statistically relevant associations.

The present invention also concerns the use of at least one of the following SNPs: g771c, 808Ins(a), in a polynucleotide of the IFNα-17 gene, for developing diagnostic/prognostic kits for a disease or a resistance to a disease.

A SNP of the invention such as defined above may be directly or indirectly associated to a disease or a resistance to a disease.

Preferably, these diseases may be those which are defined as mentioned above.

Expression Vector and Host Cells

The present invention also has for its object a recombinant vector comprising at least one polynucleotide according to the invention.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses.

These recombinant vectors can equally be cosmid or phagemid derivatives. The nucleotide sequence can be inserted in the recombinant expression vector by methods well known to a person skilled in the art such as, for example, those that are described in MOLECULAR CLONING: A LABORATORY MANUAL, Sambrook et al., 4th Ed., Cold Spring Harbor Laboratory Press, Cold Spring Harbor, N.Y., 2001.

The recombinant vector can include nucleotide sequences that control the regulation of the polynucleotide expression as well as nucleotide sequences permitting the expression and the transcription of a polynucleotide of the invention and the translation of a polypeptide of the invention, these sequences being selected according to the host cells that are used.

Thus, for example, an appropriate secretion signal can be integrated in the recombinant vector so that the polypeptide, encoded by the polynucleotide of the invention, will be directed towards the lumen of the endoplasmic reticulum, towards the periplasmic space, on the membrane or towards the extracellular environment.

The present invention also has for its object a host cell comprising a recombinant vector according to the invention.

The introduction of the recombinant vector in a host cell can be carried out according to methods that are well known to a person skilled in the art, such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as cells of streptococci, staphylococci, *E. coli* or *Bacillus subtilis*, cells of fungi such as yeast cells and cells of *Aspergillus, Streptomyces,* insect cells such as cells of *Drosophila* Sf2 and of *Spodoptera* Sf9, animal cells, such as CHO, COS, HeLa, C127, BHK, HEK 293 cells and human cells of the subject to treat or even plant cells.

The host cells can be used, for example, to express a polypeptide of the invention or as active product in pharmaceutical compositions, as will be seen hereinafter.

Polypeptide

The present invention also has for its object an isolated polypeptide comprising an amino acid sequence having at least 80% identity, preferably at least 90% identity, more preferably at least 95% identity and still more preferably at least 99% identity with all or part of:

a) the amino acid sequence SEQ ID NO. 2, or b) the amino acid sequence comprising the amino acids included between positions 24 and 189 of the amino acid sequence SEQ ID NO. 2, it being understood that each of the amino acid sequences under a) and b) contains the following coding SNP: G45R.

The polypeptide of the invention can equally comprise all or part of:

a) the amino acid sequence SEQ ID NO. 2, or b) the amino acid sequence containing the amino acids included between positions 24 and 189 of the amino acid sequence SEQ ID NO. 2, it being understood that each of the amino acid sequences under a) and b) contains the following coding SNP: G45R.

The polypeptide of the invention can more particularly consist of all or part of:

a) the amino acid sequence SEQ ID NO. 2, or b) the amino acid sequence containing the amino acids included between positions 24 and 189 of the amino acid sequence SEQ ID NO. 2, it being understood that each of the amino acid sequences under a) and b) contains the following coding SNP: G45R.

The present invention also has for its object an isolated polypeptide comprising an amino acid sequence having at least 80% identity, preferably at least 90% identity, more preferably at least 95% identity and still more preferably at least 99% identity with all or part of:

a) the amino acid sequence SEQ ID NO. 3, or b) the amino acid sequence comprising the amino acids included between positions 24 and 57 of the amino acid sequence SEQ ID NO. 3, it being understood that each of the amino acid sequences under a) and b) contains the following coding SNP: H57Q frame 57.

The polypeptide of the invention can equally comprise all or part of:

a) the amino acid sequence SEQ ID NO. 3 or b) the amino acid sequence comprising the amino acids included between positions 24 and 57 of the amino acid sequence SEQ ID NO. 3.

The polypeptide of the invention can more particularly consist of all or part of:

a) the amino acid sequence SEQ ID NO. 3, or b) the amino acid sequence comprising the amino acids included between positions 24 and 57 of the amino acid sequence SEQ ID NO. 3.

Each of the amino acid sequences under a) and b) of said polypeptide may also comprise the SNP G45R.

Preferably, a polypeptide according to the invention contains a single coding SNP selected from the group consisting of: G45R, H57Q frame 57.

More preferably, the polypeptide according to the invention comprises amino acids 24 through 189 of the amino acid sequence SEQ ID NO. 2, and has the coding SNP G45R.

More preferably, the polypeptide according to the invention comprises amino acids 24 through 57 of the amino acid sequence SEQ ID NO. 3.

The present invention equally has for its object a process for the preparation of the above-described polypeptide, in which a previously defined host cell is cultivated in a culture medium and said polypeptide is isolated from the culture medium.

The polypeptide can be purified starting from the host cells' culture medium, according to methods well known to a person skilled in the art such as precipitation with the help of chaotropic agents such as salts, in particular ammonium sulfate, ethanol, acetone or trichloroacetic acid, acid extraction; ion exchange chromatography; phosphocellulose chromatography; hydrophobic interaction chromatography; affinity chromatography; hydroxyapatite chromatography or exclusion chromatographies.

"Culture medium" is understood as the medium in which the polypeptide of the invention is isolated or purified. This medium can be composed of the extracellular medium and/or the cellular lysate. Techniques well known to a person skilled in the art equally permit the latter to give back an active conformation to the polypeptide, if the conformation of said polypeptide was altered during the isolation or the purification.

Antibodies

The present invention also has for its object a process for obtaining an immunospecific antibody.

"Antibody" is understood as the monoclonal, polyclonal, chimeric, simple chain, humanized antibodies as well as the Fab fragments, including Fab or immunoglobulin expression library products.

An immunospecific antibody can be obtained by immunization of an animal with a polypeptide according to the invention.

The invention also relates to an immunospecific antibody for a polypeptide according to the invention, such as defined previously.

A polypeptide according to the invention, one of its fragments, an analog, one of its variants or a cell expressing this polypeptide can also be used to produce immunospecific antibodies.

The term "immunospecific" means that the antibody possesses a better affinity for the polypeptide of the invention than for other polypeptides known in the prior art.

The immunospecific antibodies can be obtained by administration of a polypeptide of the invention, of one of its fragments, of an analog or of an epitopic fragment or of a cell expressing this polynucleotide in a mammal, preferably non human, according to methods well known to a person skilled in the art.

For the preparation of monoclonal antibodies, typical methods for antibody production can be used, starting from cell lines, such as the hybridoma technique (Kohler et al., Nature (1975) 256: 495-497), the trioma technique, the human B cell hybridoma technique (Kozbor et al., Immunology Today (1983) 4: 72) and the EBV hybridoma technique (Cole et al., "The EBV-hybridoma technique and its application to human lung cancer," in Monoclonal Antibodies and Cancer Therapy (Vol. 27, UCLA Symposia on Molecular and Cellular Biology, New Series) (eds. R. A. Reisfeld and S. Sell), pp. 77-96, Alan R. Liss, Inc. N.Y., 1985, pp. 77-96).

The techniques of single chain antibody production such as described, for example, in U.S. Pat. No. 4,946,778 can equally be used.

Transgenic animals such as mice, for example, can equally be used to produce humanized antibodies.

Agents Interacting with the Polypeptide of the Invention

The present invention equally has for its object a process for the identification of an agent activating or inhibiting a polypeptide according to the invention, comprising:

a) the preparation of a recombinant vector comprising a polynucleotide according to the invention containing at least one coding SNP, b) the preparation of host cells comprising a recombinant vector according to a), c) the contacting of host cells according to b) with an agent to be tested, and d) the determination of the activating or inhibiting effect generated by the agent to test.

A polypeptide according to the invention can also be employed for a process for screening compounds that interact with it.

These compounds can be activating (agonists) or inhibiting (antagonists) agents of intrinsic activity of a polypeptide according to the invention. These compounds can equally be ligands or substrates of a polypeptide of the invention. See Coligan et al., Current Protocols in Immunology 1 (2), Chapter 5 (1991).

In general, in order to implement such a process, it is first desirable to produce appropriate host cells that express a polypeptide according to the invention. Such cells can be, for example, cells of mammals, yeasts, insects such as *Drosophila* or bacteria such as *E. coli*.

These cells or membrane extracts of these cells are then put in the presence of compounds to be tested.

The binding capacity of the compounds to be tested with the polypeptide of the invention can then be observed, as well as the inhibition or the activation of the functional response.

Step d) of the above process can be implemented by using an agent to be tested that is directly or indirectly labeled. It can also include a competition test, by using a labeled or non-labeled agent and a labeled competitor agent.

It can equally be determined if an agent to be tested generates an activation or inhibition signal on cells expressing the polypeptide of the invention by using detection means appropriately chosen according to the signal to be detected.

Such activating or inhibiting agents can be polynucleotides, and in certain cases oligonucleotides or polypeptides, such as proteins or antibodies, for example.

The present invention also has for its object a process for the identification of an agent activated or inhibited by a polypeptide according to the invention, comprising:

a) the preparation of a recombinant vector comprising a polynucleotide according to the invention containing at least one coding SNP, b) the preparation of host cells comprising a recombinant vector according to a), c) placing host cells according to b) in the presence of an agent to be tested, and d) the determination of the activating or inhibiting effect generated by the polypeptide on the agent to be tested.

An agent activated or inhibited by the polypeptide of the invention is an agent that responds, respectively, by an activation or an inhibition in the presence of this polypeptide.

The agents, activated or inhibited directly or indirectly by the polypeptide of the invention, can consist of polypeptides such as, for example, membranal or nuclear receptors, kinases and more preferably tyrosine kinases, transcription factors or polynucleotides.

Detection of Diseases

The present invention also has for object a process for analyzing the biological characteristics of a polynucleotide according to the invention and/or of a polypeptide according to the invention in a subject, comprising at least one of the following:

a) Determining the presence or the absence of a polynucleotide according to the invention in the genome of a subject;

b) Determining the level of expression of a polynucleotide according to the invention in a subject;

c) Determining the presence or the absence of a polypeptide according to the invention in a subject;

d) Determining the concentration of a polypeptide according to the invention in a subject; and/or e) Determining the functionality of a polypeptide according to the invention in a subject.

These biological characteristics may be analyzed in a subject or in a sample from a subject.

These biological characteristics may permit to carry out a genetic diagnosis and to determine whether a subject is affected or at risk of being affected or, to the contrary, presents a partial resistance to the development of a disease, an indisposition or a disorder linked to the presence of a polynucleotide according to the invention and/or a polypeptide according to the invention.

These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

This process also permits genetic diagnosis of a disease or of a resistance to a disease linked to the presence, in a subject, of the mutant allele encoded by a SNP according to the invention.

Preferably, in step a), the presence or absence of a polynucleotide, containing at least one coding SNP such as previously defined, is going to be detected.

The detection of the polynucleotide may be carried out starting from biological samples from the subject to be studied, such as cells, blood, urine, saliva, or starting from a biopsy or an autopsy of the subject to be studied. The genomic DNA may be used for the detection directly or after a PCR amplification, for example. RNA or cDNA can equally be used in a similar fashion.

It is then possible to compare the nucleotide sequence of a polynucleotide according to the invention with the nucleotide sequence detected in the genome of the subject.

The comparison of the nucleotide sequences can be carried out by sequencing, by DNA hybridization methods, by mobility difference of the DNA fragments on an electrophoresis gel with or without denaturing agents or by melting temperature difference (see Myers et al., Science (1985) 230: 1242). Such modifications in the structure of the nucleotide sequence at a precise point can equally be revealed by nuclease protection tests, such as RNase and the S1 nuclease, by enzymatic digestion or also by chemical cleaving agents. See Cotton et al., Proc. Nat. Acad. Sci. USA (1985) 85: 4397-4401. Oligonucleotide probes comprising a polynucleotide fragment of the invention can equally be used to conduct the screening.

Many methods well known to a person skilled in the art can be used to determine the expression of a polynucleotide of the invention and to identify the genetic variability of this polynucleotide (See Chee et al., Science (1996), Vol 274, pp 610-613).

In step b), the level of expression of the polynucleotide may be measured by quantifying the level of RNA encoded by this polynucleotide (and coding for a polypeptide) according to methods well known to a person skilled in the art as, for example, by PCR, RT-PCR, RNase protection, Northern blot, and other hybridization methods.

In step c) and d) the presence or the absence as well as the concentration of a polypeptide according to the invention in a subject or a sample from a subject may be carried out by well known methods such as, for example, by radioimmunoassay, competitive binding tests, Western blot and ELISA tests.

Consecutively to step d), the determined concentration of the polypeptide according to the invention can be compared with the natural wild-type protein concentration usually found in a subject.

A person skilled in the art can identify the threshold above or below which appears the sensitivity or, to the contrary, the resistance to the disease, the indisposition or the disorder evoked above, with the help of prior art publications or by conventional tests or assays, such as those that are previously mentioned.

In step e), the determination of the functionality of a polypeptide according to the invention may be carried out by methods well known to a person skilled in the art as, for example, by in vitro tests such as above mentioned or by any use of host cells expressing said polypeptide.

Therapeutic Compounds and Treatments of Diseases

The present invention also has for its object a therapeutic compound containing, by way of active agent, a polypeptide according to the invention.

The invention also relates to the use of a polypeptide according to the invention, for the manufacture of a therapeutic compound intended for the prevention or the treatment of different human disorders and/or diseases. These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

Preferably, a polypeptide according to the invention can also be used for the manufacture of a therapeutic compound intended for the prevention or the treatment of different human disorders and/or diseases, such as certain viral infections such as chronic hepatitis B and C, leukemias such as hairy-cell leukemia and chronic myeloid leukemia, multiple myelomas, follicular lymphomas, carcinoid tumors, malignant melanomas, metastasizing renal carcinomas, Alzheimer's disease, Parkinson's disease, as well as tumors that appear following an immune deficiency, such as Kaposi's sarcoma in the case of AIDS, and genital warts or venereal diseases.

Certain of the compounds permitting to obtain the polypeptide according to the invention as well as the compounds obtained or identified by or from this polypeptide can likewise be used for the therapeutic treatment of the human body, i.e. as a therapeutic compound.

This is why the present invention also has for an object a medicament containing, by way of active agent, a polynucleotide according to the invention containing at least one previously defined coding SNP, a previously defined recombinant vector, a previously defined host cell, and/or a previously defined antibody.

The invention also relates to the use of a polynucleotide according to the invention containing at least one previously defined coding SNP, a previously defined recombinant vector, a previously defined host cell, and/or a previously defined antibody for the manufacture of a medicament intended for the prevention or the treatment of different human disorders and/or diseases. These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

Preferably, the invention concerns the use of a polynucleotide according to the invention containing at least one previously defined SNP, a previously defined recombinant vector, a previously defined host cell, and/or a previously defined antibody, for the manufacture of a medicament intended for the prevention or the treatment of different human disorders and/or diseases, such as certain viral infections such as chronic hepatitis B and C, leukemias such as hairy-cell leukemia and chronic myeloid leukemia, multiple myelomas, follicular lymphomas, carcinoid tumors, malignant melanomas, metastasizing renal carcinomas, Alzheimer's disease, Parkinson's disease, as well as tumors that appear following an immune deficiency, such as Kaposi's sarcoma in the case of AIDS, and genital warts or venereal diseases.

The dosage of a polypeptide and of the other compounds of the invention, useful as active agent, depends on the choice of the compound, the therapeutic indication, the mode of administration, the nature of the formulation, the nature of the subject and the judgment of the doctor.

When it is used as active agent, a polypeptide according to the invention is generally administered at doses ranging between 1 and 15 M IU (International Unit). The recommended dose may be administered either by subcutaneous or intramuscular route, between 1 to 5 times a week, for 1 to 12 months.

The invention also has as an object a pharmaceutical composition that contains, as active agent, at least one above-mentioned compound such as a polypeptide according to the invention, a polynucleotide according to the invention containing at least one previously defined SNP, a previously defined recombinant vector, a previously defined host cell, and/or a previously defined antibody, as well as a pharmaceutically acceptable excipient.

In these pharmaceutical compositions, the active agent is advantageously present at physiologically effective doses.

These pharmaceutical compositions can be, for example, solids or liquids and be present in pharmaceutical forms currently used in human medicine such as, for example, simple or coated tablets, gelcaps, granules, caramels, suppositories and preferably injectable preparations and powders for injectables. These pharmaceutical forms can be prepared according to usual methods.

The active agent(s) can be incorporated into excipients usually employed in pharmaceutical compositions such as talc, Arabic gum, lactose, starch, dextrose, glycerol, ethanol, magnesium stearate, cocoa butter, aqueous or non-aqueous vehicles, fatty substances of animal or vegetable origin, paraffinic derivatives, glycols, various wetting agents, dispersants or emulsifiers, preservatives.

The active agent(s) according to the invention can be employed alone or in combination with other compounds such as therapeutic compounds such as other cytokines such as interleukins or interferons, for example.

The different formulations of the pharmaceutical compositions are adapted according to the mode of administration.

The pharmaceutical compositions can be administered by different routes of administration known to a person skilled in the art.

The invention equally has for an object a diagnostic composition that contains, as active agent, at least one above-mentioned compound such as a polypeptide according to the invention, all or part of a polynucleotide according to the invention, a previously defined recombinant vector, a previously defined host cell, and/or a previously defined antibody, as well as a suitable pharmaceutically acceptable excipient.

This diagnostic composition may contain, for example, an appropriate excipient like those generally used in the diagnostic composition such as buffers and preservatives.

The present invention equally has as an object the use:

a) of a therapeutically effective quantity of a polypeptide according to the invention, and/or b) of a polynucleotide according to the invention, and/or c) of a host cell from the subject to be treated, previously defined, to prepare a therapeutic compound intended to increase the expression or the activity, in a subject, of a polypeptide according to the invention.

Thus, to treat a subject who needs an increase in the expression or in the activity of a polypeptide of the invention, several methods are possible.

It is possible to administer to the subject a therapeutically effective quantity of a polypeptide of the invention, with a pharmaceutically acceptable excipient.

It is likewise possible to increase the endogenous production of a polypeptide of the invention by administration to the subject of a polynucleotide according to the invention. For example, this polynucleotide can be inserted in a retroviral expression vector. Such a vector can be isolated starting from cells having been infected by a retroviral plasmid vector containing RNA encoding for the polypeptide of the invention, in such a fashion that the transduced cells produce infectious viral particles containing the gene of interest. See Gene Therapy and other Molecular Genetic-based Therapeutic Approaches, Chapter 20, in Human Molecular Genetics, Strachan and Read, BIOS Scientifics Publishers Ltd (1996).

In accordance with the invention, a polynucleotide containing at least one coding SNP such as previously defined will be preferably used.

It is equally possible to administer to the subject host cells belonging to him, these host cells having been preliminarily taken and modified so as to express the polypeptide of the invention, as previously described.

The present invention equally relates to the use:
  a) of a therapeutically effective quantity of a previously defined immunospecific antibody, and/or
  b) of a polynucleotide permitting inhibition of the expression of a polynucleotide according to the invention,
in order to prepare a therapeutic compound intended to reduce the expression or the activity, in a subject, of a polypeptide according to the invention.

Thus, it is possible to administer to the subject a therapeutically effective quantity of an inhibiting agent and/or of an antibody such as previously defined, possibly in combination, with a pharmaceutically acceptable excipient.

It is equally possible to reduce the endogenous production of a polypeptide of the invention by administration to the subject of a complementary polynucleotide according to the invention permitting inhibition of the expression of a polynucleotide of the invention.

Preferably, a complementary polynucleotide containing at least one coding SNP such as previously defined can be used.

The present invention concerns also the use of a IFNα-17 protein for the preparation of a medicament for the prevention or the treatment of a patient having a disorder or a disease caused by a IFNα-17 variant linked to the presence in the genome of said patient of a nucleotide sequence having at least 95% identity (preferably, 97% identity, more preferably 99% identity and particularly 100% identity) with the nucleotide sequence SEQ ID NO. 1, provided that said nucleotide sequence comprises one of the following SNPs: g771c, 808Ins(a).

Preferably, said medicament is used for the prevention or the treatment of one of the diseases selected from the group consisting of cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

Mimetic Compounds of an IFNα-17 Polypeptide Comprising the SNP g771c of the Invention The present invention also concerns a new compound having a biological activity substantially similar to that of the polypeptide of:
  a) amino acid sequence SEQ ID NO. 2, or
  b) amino acid sequence comprising the amino acids included between positions 24 and 189 of the amino acid sequence SEQ ID NO. 2;
  provided that said amino acid sequences under a) and b) comprise the SNP G45R.

Said biological activity may be evaluated, for example, by measuring dendritic cell maturation, cytokine release by CD4+ or CD8+ T-lymphocytes, cytokine release by monocytes, in vitro or in vivo antiviral activity, cellular antiproliferative activity on TF-1 cell line, or cellular antiproliferative activity on Daudi Burkitt's cell line as described in the experimental part.

As mentioned in the experimental section, in comparison to wild-type IFNα-2, the G45R mutated IFNα-17 possesses:
  a higher capacity to stimulate IFN-gamma release by CD4+ T-lymphocytes
  a higher capacity to stimulate IFN-gamma and IL-10 release by CD8+ T-lymphocytes
  a lower capacity to stimulate IL-10 and IL-12 release by monocytes
  a similar antiproliferative activity on TF-1 cells
  a higher antiproliferative activity on Daudi Burkitt's cell line cells
  a higher antiviral activity in vitro in cell culture infected with VS
  a higher antiviral activity in vivo in EMCV mouse model.

As mentioned in the experimental section too, the G45R mutated IFNα-17 possesses a lower cellular antiproliferative activity on Daudi Burkitt's cell line in comparison to that of wild-type IFNα-17.

A new compound of the invention, such as previously defined, may possess a biological activity substantially similar to that of the G45R mutated IFNα-17.

Said compound may also have a biological activity such as IFN-gamma release by CD4+ or CD8+ T-lymphocytes, IL-10 release by CD8+ T-lymphocytes, antiviral activity in vitro, or antiviral activity in vivo, which is even higher than that of the G45R mutated IFNα-17.

Said compound may also have a biological activity such as IL-10 and IL-12 release by monocytes, which is even lower than that of the G45R mutated IFNα-17.

Said compound may be a biochemical compound, such as a polypeptide or a peptide for example, or an organic chemical compound, such as a synthetic peptide-mimetic for example.

The present invention also concerns the use of a polypeptide of the invention containing the G45R SNP, for the identification of a compound such as defined above.

The present invention also concerns a process for the identification of a compound of the invention, comprising the following steps:

a) Determining the biological activity of the compound to be tested, such as dendritic cell maturation, cytokine release by CD4+ or CD8+ T-lymphocytes, cytokine release by monocytes, cellular antiproliferative activity on TF-1 cell line, cellular antiproliferative activity on Daudi Burkitt's cell line, in vitro or in vivo antiviral activity, for example;

b) Comparing:

i) the activity determined in step a) of the compound to be tested, with ii) the activity of the polypeptide of amino acid sequence SEQ ID NO. 2, or of amino acid sequence comprising the amino acids included between positions 24 and 189 of the amino acid sequence SEQ ID NO. 2; provided that said amino acid sequences comprise the G45R SNP; and c) Determining on the basis of the comparison carried out in step b) whether the compound to be tested has a substantially similar, or lower or higher, activity compared to that of the polypeptide of amino acid sequence SEQ ID NO. 2, or of amino acid sequence comprising the amino acids included between positions 24 and 189 of the amino acid sequence SEQ ID NO. 2; provided that said amino acid sequences comprise the G45R SNP.

Preferably, the compound to be tested may be previously identified from synthetic peptide combinatorial libraries, high-throughput screening, or designed by computer-aided drug design so as to have the same three-dimensional structure as that of the polypeptide of amino acid sequence SEQ ID NO. 2, or of amino acid sequence comprising the amino acids included between positions 24 and 189 of the amino acid sequence SEQ ID NO. 2; provided that said amino acid sequences comprise the G45R SNP.

The methods to identify and design compounds are well known by a person skilled in the art.

Publications referring to these methods may be, for example:

Silverman R. B. (1992). "Organic Chemistry of Drug Design and Drug Action". Academic Press, 1st edition (Jan. 15, 1992).

Anderson S and Chiplin J. (2002). "Structural genomics; shaping the future of drug design" Drug Discov. Today. 7(2):105-107.

Selick H E, Beresford A P, Tarbit M H. (2002). "The emerging importance of predictive ADME simulation in drug discovery". Drug Discov. Today. 7(2):109-116.

Burbidge R, Trotter M, Buxton B, Holden S. (2001). "Drug design by machine learning: support vector machines for pharmaceutical data analysis". Comput. Chem. 26(1): 5-14.

Kauvar L. M. (1996). "Peptide mimetic drugs: a comment on progress and prospects" 14(6): 709.

The compounds of the invention may be used for the preparation of a medicament intended for the prevention or the treatment of one of the diseases selected from the group consisting of cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

Preferably, the compounds of the invention may be used for the preparation of a medicament intended for the prevention or the treatment of one of the diseases selected from the group consisting of certain viral infections such as chronic hepatitis B and C, leukemias such as hairy-cell leukemia and chronic myeloid leukemia, multiple myelomas, follicular lymphomas, carcinoid tumors, malignant melanomas, metastasizing renal carcinomas, Alzheimer's disease, Parkinson's disease, as well as tumors that appear following an immune deficiency, such as Kaposi's sarcoma in the case of AIDS, and genital warts or venereal diseases.

EXPERIMENTAL SECTION

EXAMPLE 1

Modeling of a Protein Encoded by a Polynucleotide of Nucleotide Sequence Containing SNP G45R and of the Protein Encoded by the Nucleotide Sequence of the Wild-Type Reference Gene In a first step the three-dimensional structure of IFNα-17 was constructed starting from that of IFNα-2 whose structure is available in the PDB database (code 1ITF) and by using the software Modeler (MSI, San Diego, Calif.).

The mature polypeptide fragment was then modified in such a fashion as to reproduce the mutation G45R.

A thousand molecular minimization steps were conducted on this mutated fragment by using the programs AMBER and DISCOVER (MSI: Molecular Simulations Inc.).

Two molecular dynamic calculation runs were then carried out with the same program and the same force fields.

In each case, 50,000 steps were calculated at 300° K., terminated by 300 equilibration steps.

The result of this modeling is visualized on FIGS. 1A and 1B.

EXAMPLE 2

Expression of Natural Wild-Type IFNα-17 and G45R Mutated IFNα-17 in Yeast a) Cloning of the Natural Wild-Type IFNα-17 and Mutated IFNα-17 in the Eukaryote Expression Vector pPicZα-Topo The nucleotide sequences coding for the mature part of the natural wild-type IFNα-17 and G45R mutated IFNα-17 are amplified by PCR using as template genomic DNA from an individual who is heterozygote for the SNP.

The PCR primers permitting such an amplification are:
SEQ ID NO. 6: Sense primer: TGTGATCTGCCTCAGACCCAC
SEQ ID NO. 7: Antisense primer: TCAATCCTTCCTCCTTAATATTTTTGC The PCR products are inserted in the eukaryote expression vector pPicZα-TOPO under the control of the hybrid promoter AOX1 inducible by methanol (TOPO™-cloning; Invitrogen Corp.).

This vector permits the heterologous expression of eukaryote proteins in the yeast *Pichia pastoris*.

After checking of the nucleotide sequence of the region of the vector coding for the recombinant proteins, the vector is linearized by the Pme1 restriction enzyme, and the *P. pastoris* yeast strain (Invitrogen) is transformed with these recombinant expression vectors.

b) Heterologous Expression in *P. pastoris* and Purification of the Wild-Type IFNα-17 and G45R Mutated IFNα-17 Proteins Two saturated pre-cultures of 50 mL of BMGY medium (2% Peptone, 1% yeast extract, 1.34% YNB, 1% Glycerol, 100 mM potassium phosphate, 0.4 mg/Liter biotin pH 6.0) containing a clone coding for wild-type IFNα-17 protein or that coding for G45R mutated IFNα-17 protein, were carried out for 24-48 hours at 30° C. at an agitation of 200 rotations per minute (rpm).

When the culture reaches a saturating cellular density (corresponding to an optical density of 12 measured at a wavelength of 600 nm), it is used to inoculate, at 5 OD/mL, 250 mL of BMMY medium (2% Peptone, 1% yeast extract, 1.34% YNB, 0.5% Methanol, 100 mM potassium phosphate, 0.4 mg/Liter biotin pH 6.0).

The expression of the protein is then induced by methanol at a final concentration of 1%, for 24 hours at 30° C., with an agitation of the culture flask at 180 rpm.

Due to the presence of the signal peptide sequence of the "alpha factor", upstream of the coding sequence, the proteins are secreted by the yeasts in the culture medium. The alpha factor is naturally cleaved during the processing.

The suspension is centrifuged and the protein is purified by HPLC starting from the obtained supernatant.

In a pre-started step, an ultrafiltration (Labscale, cut-off 5000 Da, Millipore) followed by a dialysis permits a ten times concentration of the yeast supernatant in a buffer of 50 mM Tris-Cl pH 9.0, 25 mM NaCl.

The first chromatographic step permits protein recovery by affinity on a blue sepharose column (Amersham Pharmacia). The presence of the protein in the collected fractions is verified, on the one hand by electrophoresis of SDS PAGE type and on the other hand by immuno-detection by a specific antibody directed against the IFNα-17 protein. At this step, the purity of the protein of interest is higher than 75%.

In a second purification step, a gel filtration permits buffer exchange of the collected fractions corresponding to IFNα-17 proteins against 50 mM Tris pH 9.0, 25 mM NaCl.

The last step of the purification consists of a separation of the proteins on an ion exchange chromatography column.

The fractions containing the recombinant protein are injected on an anion exchange column (ResourceQ 6.0 mL, Pharmacia) equilibrated beforehand in Tris 50 mM pH 9, NaCl 25 mM buffer. The elution of the proteins is carried out by the migration of a gradient between 0.025 and 1 M NaCl in the Tris 50 mM pH 9 buffer.

The purity of the protein of interest is estimated on SDS/PAGE gel and the protein concentrations were measured by densitometry (Quantity one, Biorad) and BCA assay (bicinchoninic acid and copper sulfate, Sigma).

Purified wild-type IFNα-17 and G45R mutated IFNα-17 proteins obtained according to this protocol, eventually scaled-up to produce higher amount of proteins, are used for the functional tests described below.

EXAMPLE 3

Evaluation of Immunomodulatory Activity of Natural Wild-Type IFNα-17 and G45R Mutated IFNα-17

IFNs type I (IFN alpha and IFN beta) are able to modulate certain functions of the immune system. They have been demonstrated to increase the dendritic cells (DC) maturation: increase in the expression of MHC class I (HLA-ABC) and II (HLA-DR) molecules, increase in the expression of the molecules involved in the co-stimulation of the T-lymphocytes, CD80, CD86 and CD83 molecules and increase in the stimulating function of T-lymphocytes.

Effect of G45R mutated IFNα-17 on dendritic cell maturation.

Immunomodulatory activity of G45R mutated IFNα-17 was first investigated on dendritic cells maturation and compared to that of wild-type IFNα-2 chosen as representative of commercial Intron A product.

To do so, dendritic cells were first generated from adult peripheral blood monocytes cultivated in the presence of GM-CSF and IL-4 cytokines. After purification using a CD14+ cells purification kit, these dendritic cells were placed in presence of 100 ng/mL of wild-type IFNα-2 or G45R mutated IFNα-17 and their phenotype was determined by FACS analysis aiming at looking for the expression of the MHC class I and II molecules and the CD40, CD80, CD86, CD83 and CD1a markers. The maturation state of these dendritic cells has also been compared to that obtained without IFNα treatment, to provide a control with non-stimulated dendritic cells.

The median value of the measures of fluorescence intensity for each marker and for the three experimental conditions, expressed as arbitrary unit, are presented in the following table:

| | HLA ABC | HLA DR | CD40 | CD80 | CD86 | CD83 | CD1a |
|---|---|---|---|---|---|---|---|
| No IFNα | 142 | 155 | 246 | 40 | 24 | 21 | 65 |
| G45R mutated IFNα-17 | 165 | 189 | 316 | 50 | 32 | 19 | 49 |
| Wild-type IFNα-2 | 179 | 276 | 491 | 87 | 57 | 26 | 51 |

The results of this test demonstrate that the G45R mutated IFNα-17 protein is able to stimulate dendritic cell maturation.

Effect of G45R mutated IFNα-17 on cytokine release by T lymphocytes

Immunomodulatory activity of G45R mutated IFNα-17 was also investigated by measuring cytokine release by T lymphocytes placed in presence of mutated IFNα-17 protein and with or without a strong antigen (SEB) in order to mimic an immune response against an aggression. This test was also performed in presence of wild-type IFNα-2 used as control and chosen as representative of the Intron A commercial product.

To do so, peripheral blood mononuclear cells (PBMC) were isolated from healthy donors and stimulated for 16 hours in an appropriate medium containing anti-CD3 and anti-CD28 antibodies or SEB. In each culture was added 4 μg/mL of wild-type IFNα-2 or G45R mutated IFNα-17. After stimulation, T lymphocytes were extracellularly labeled with anti-CD3, anti-CD4 and anti-CD69 antibodies or anti-CD3, anti-CD8 and anti-CD69 antibodies, and intracellularly labeled with specific antibodies directed against Th1-type cytokines (IFN-gamma) or Th2-type cytokines (IL-10). Fluorescent cells were analysed using FACSCALIBUR and CELLQUEST software.

The results obtained indicate that G45R mutated IFNα-17 and wild-type IFNα-2 do not stimulate IL-10 and IFN-gamma release and, thus, do not activate T lymphocytes in absence of SEB.

In contrast, G45R mutated IFNα-17 and wild-type IFNα-2 stimulate cytokines (IL-10 and IFN-gamma) release by SEB-activated T-lymphocytes as shown in the table below. This table represents the cytokine release by T-lymphocytes in presence of SEB, expressed as percentage of the CD4+ CD69+ cells or CD8+ CD69+ cells for the CD4+ T-lymphocytes and CD8+ T-lymphocytes, respectively, and the percentage of CD69+ cells on total cells.

| T-lymphocyte | | IFN gamma | IL-10 | CD69+ cells/total |
|---|---|---|---|---|
| CD4+ CD69+ | Negative control | 11.9 | 7.5 | 1.26 |
| | G45R IFNα-17 | 37.27 | 20.06 | 2.94 |
| | Wild-type IFNα-2 | 19.6 | 24.68 | 2.7 |
| CD8+ CD69+ | Negative control | 8.73 | 0.65 | 4.69 |
| | G45R IFNα-17 | 36.7 | 7.02 | 9.54 |
| | Wild-type IFNα-2 | 16.37 | 4.26 | 10.02 |

These results clearly demonstrate that G45R mutated IFNα-17 strongly stimulates cytokine release (IFN gamma and IL-10) by CD4+ T-lymphocytes and CD8+ T-lymphocytes previously activated by SEB antigen. In this test, the interferon gamma production by CD4+ T-lymphocytes is higher in presence of G45R mutated IFNα-17 than in presence of wild-type IFNα-2 and the interferon gamma and IL-10 production by CD8+ T-lymphocytes is higher in presence of G45R mutated IFNα-17 than in presence of wild-type IFNα-2.

Effect of G45R mutated IFNα-17 on cytokine release by monocytes

Finally, immunomodulatory activity of G45R mutated IFNα-17 was investigated by measuring cytokine release by monocytes in absence or in presence of a bacterial toxic agent (LPS). This test was also performed in presence of wild-type IFNα-2 used as control and chosen as representative of the Intron A commercial product.

To do so, human peripheral blood mononuclear cells (PBMC) were isolated from healthy donors and their phenotype was analyzed to determine the relative amount of CD64+ CD4dim cells (CD64 and CD4dim are markers for blood monocytes). After an over-night culture, these PBMC were incubated in the culture medium alone (not stimulated cells) or in presence of LPS (stimulated cells). In each culture, 4 μg/mL of wild-type IFNα-2 or G45R mutated IFNα-17 was added. After culture, cells were extracellularly labelled with anti-CD64 and anti-CD4dim, and intracellularly labelled with specific antibodies directed against Th1-type cytokines (TNF-alpha), IL-12 and IL-10.

Fluorescent cells were analyzed using FACSCALIBUR and CELLQUEST software.

The results obtained indicate that G45R mutated IFNα-17 and wild-type IFNα-2 do not stimulate cytokines (IL-10, IL-12 and TNF-alpha) release in absence of LPS.

In contrast, in presence of LPS, monocytes release cytokines. The IL-10 and IL-12 release by monocytes in presence of LPS is further increased in presence of wild-type IFNα-2 but not in presence of G45R mutated IFNα-17 as shown in the table below. This table represents cytokine release by monocytes in presence of LPS, expressed as percentage of the CD64+ CD4dim cells, and the percentage of CD4dim CD64+ cells on total cells.

| | IL-10 | IL-12 | TNF-α | CD4dim CD64+ cells/total |
|---|---|---|---|---|
| No IFNα | 16.21 | 8.52 | 13.88 | 3.1 |
| G45R IFNα-17 | 17.47 | 8.3 | 40.92 | 2.86 |
| Wild-type IFNα-2 | 49.34 | 34.48 | 50.87 | 2.71 |

Thus, the absence of synergetic effect observed in presence of G45R mutated IFNα-17 and LPS suggests that G45R mutated IFNα-17 may have an immunosuppressive action.

EXAMPLE 4

Evaluation of In Vitro Antiproliferative Activity of G45R Mutated IFNα-17 on the TF-1 Erythroleukemia Cell Line The effect of G45R mutated IFNα-17 was also evaluated on TF-1 erythroleukemia cell line. This test was also performed in presence of wild-type IFNα-2 used as control and chosen as representative of the Intron A commercial product.

To do so, TF-1 cells were placed in contact of increasing concentrations of mutated IFNα-21 or wild-type IFNα-2 (0.001 to 1000 ng/mL) and the cell proliferation measured.

The results, presented in FIG. 2, indicate that the G45R mutated IFNα-17 has a weak antiproliferative effect on TF-1 cells, and this effect is similar to that of wild-type IFNα-2, suggesting that the G45R mutated IFNα-17's hematologic toxicity is not superior than that of wild-type IFNα-2.

EXAMPLE 5

Evaluation of the Capacity of G45R Mutated IFNα-17 to Induce the Anti-Proliferation of the Human Daudi Burkitt's Lymphoma Cell Line These tests are carried out on two different IFNα-17 proteins, namely G45R mutated IFNα-17 and natural wild-type IFNα-17. Cells (human Daudi Burkitt's lymphoma cell line, hereinafter called "Daudi cells") cultivated beforehand in a RPMI 1640 medium (supplemented with 10% fetal calf serum and 2 mM of L-Glutamine) are inoculated in 96 well plates at the cellular density of $4.10^4$ cells/well.

In each well, Daudi cells are placed in contact of increasing concentrations of: either natural wild-type IFNα-17 or G45R mutated IFNα-17 proteins.

The concentrations of IFNα-17 studied (natural wild-type or mutated protein) are included between 0.003 pM and 600 nM (final concentrations in the wells).

The Daudi cells are then incubated for 66 h at 37° C. under 5% $CO_2$ after which the Uptiblue reagent (Uptima) is added to the cultures. The rate of cell proliferation is quantified by measuring the fluorescence emitted at 590 nm (excitation 560 nm) after an additional period of incubation of 4 hours.

The anti-proliferative activity of natural wild-type IFNα-17 or G45R mutated IFNα-17 is based on the measurements of the IC50, corresponding to the concentration of IFNα-17 protein, in picomolar (pM), inhibiting 50% of cellular growth.

Four similar experiments were carried out, each being repeated four times. For each experiment, the IC50 values are mentioned in the following table:

| | IC50 (pM) | | |
|---|---|---|---|
| Experiment | Wild-typ IFNα-17 | G45R IFNα-17 | Ratio |
| 1 | 0.32 | 1.51 | 5 |
| 2 | 0.60 | 7.20 | 12 |
| 3 | 0.22 | 1.53 | 7 |
| 4 | 0.81 | 10.99 | 14 |

The average IC50 value measured for the wild-type IFNα-17 is 0.49 pM, whereas the average IC50 value measured for the G45R mutated IFNα-17 is 5.31 pM. Thus, the average ratio corresponding to the value of the IC50 for the mutated IFNα-17 over the value for the natural wild-type IFNα-17 reaches 10.80 (with a standard deviation of 3.46).

This test demonstrates that the cellular antiproliferative activity is strongly inhibited (approximately in a range comprised between 5 to 15 times less) in the case of G45R mutated IFNα-17 by comparison with wild-type IFNα-17.

Similar independent experiments have also been performed with wild-type IFNα-2 in order to compare the antiproliferative effect of G45R mutated IFNα-17 on Daudi cells proliferation with the effect of wild-type IFNα-2. To do so, Daudi cells were cultivated in the presence of concentrations of G45R mutated IFNα-17 or wild-type IFNα-2 ranging from 0.001 to 10 ng/mL.

Figure 3:
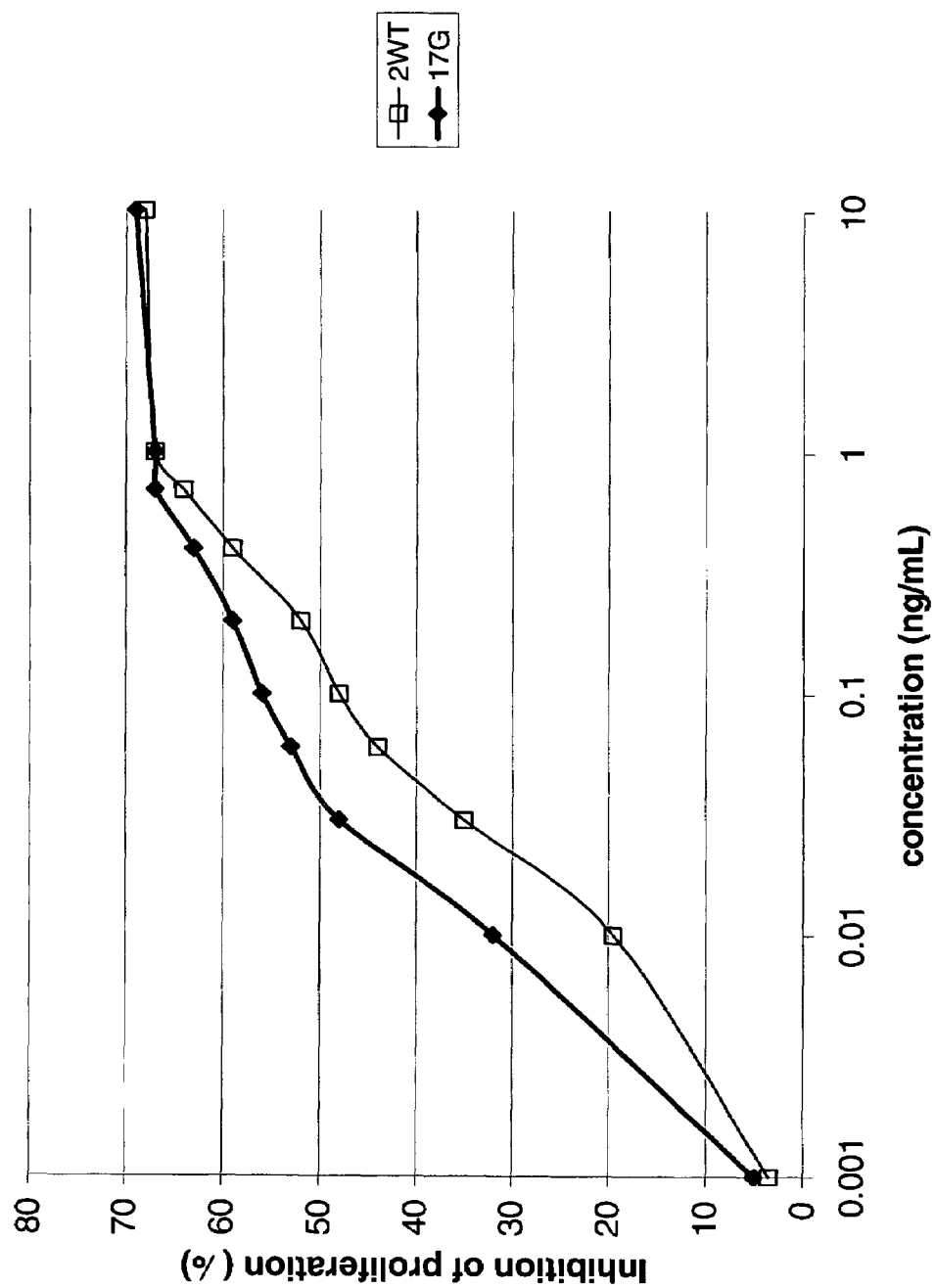
FIG. 3 represents the results of the test for measuring the antiproliferative effect of G45R mutated IFNα-17, on the Daudi Burkitt's cell line. In this figure, the abscissas correspond to the concentration of IFNα (ng/mL) and the ordinates correspond to the inhibition of cell proliferation (%). The antiproliferative effect of the G45R mutated IFNα-17 (black diamonds) is compared to that of wild-type IFNα-2 (white squares).

Three similar experiments were carried out. The results of one representative experiment are presented in FIG. 3.

These results demonstrate that the cellular antiproliferative activity of G45R mutated IFNα-17 on Daudi Burkitt's cell line is higher than that of wild-type IFNα-2.

EXAMPLE 6

Evaluation of the Antiviral Activity of G45R Mutated IFNα-17

The IFNs play an important role in the antiviral defence. The IFN antiviral activity is partly due to IFNs induced enzymatic systems, such as:

The 2'5' oligoadenylate synthetase, an enzyme which catalyzes the adenosine oligomere synthesis. These oligomeres activate the RNase L, an endoribonuclease which destroy the viral RNA once activated.

The Mx proteins (GTPases) which inhibit the synthesis and/or the maturation of viral transcripts. This activity is mainly exerted on the influenza virus.

The PKR protein (or p68 kinase) which is activated by the double-stranded RNA. The activated PKR inhibits protein synthesis.

The IFNs antiviral activity is also induced by other mechanisms such as, in the case of retroviruses, the inhibition of viral particles entry into the cells, the replication, the binding, the exit of the particles and the infective power of viral particles.

Finally, the IFNs exert an indirect antiviral activity by modulating certain functions of the immune system, in particular by favoring the response to cellular mediation (including an increase of the MHC class I and II molecules, increase of IL-12 and IFN-gamma production, increase of the CTL activities, among others).

The antiviral activity of G45R mutated IFNα-17 has been evaluated both in vitro in cell culture and in vivo in mouse model. Both tests have been carried out in parallel with wild-type IFNα-2 used as control and chosen as representative of the Intron A commercial product.

a) Antiviral Activity In Vitro in Cell Culture

This assay permits evaluation of the antiviral activity of G45R mutated IFNα-17 and wild-type IFNα-2 in cell culture using the vesicular stomatitis virus (VSV).

To do so, WISH human epithelial cells are cultivated for 24 hours in the presence of decreasing concentrations of G45R mutated IFNα-17 or wild-type IFNα-2. Then, the cells are infected by the virus of vesicular stomatitis (VSV) during 24 to 48 additional hours and the cell lysis is measured.

The antiviral effect of the different IFNα tested is determined by comparing the IC50 value corresponding to the IFN concentration inhibiting 50% of cell lysis induced by the VSV.

A similar experiment has been carried out two times, and the IC50 values measured in one representative experiment are presented in the following table:

| | Wild-type IFNα-2 | G45R mutated IFNα-17 |
|---|---|---|
| IC50 (ng/mL) | 4 | 2 |

Thus, in cell culture infected with VSV, the G45R mutated IFNα-17 exhibits an antiviral activity, this antiviral activity being higher than that of wild-type IFNα-2.

b) Antiviral Activity In Vivo in Mouse Model

This test in vivo is performed in EMCV (Encephalomyocarditis virus) mouse model.

Human IFNs exhibit dose-dependent antiviral activity in the mouse which is in general 100 to 1,000 fold less than that exhibited by the same amount of mouse IFN (Meister et al. (1986). J. Gen. Virol. 67, 1633-1644).

Intraperitoneal injection of mice with Encephalomyocarditis virus (EMCV) gives rise to a rapidly progressive fatal disease characterized by central nervous system involvement and encephalitis (Finter NB (1973). Front Biol. 2: 295-360). Mouse and human interferon-alpha have both been shown to be effective in protecting mice against lethal EMCV infection (Tovey and Maury (1999). J. IFN Cytokine Res. 19: 145-155).

Groups of 20, six-week old Swiss mice were infected intraperitoneally (ip) with 100× $LD_{50}$ EMCV and treated one hour later, and then once daily for 3 days thereafter with 2 μg of G45R mutated IFNα-17 or wild-type IFNα-2 preparations. A control group was performed with animals having been treated with excipient only. The animals were followed daily for survival for 21 days.

Figure 4:
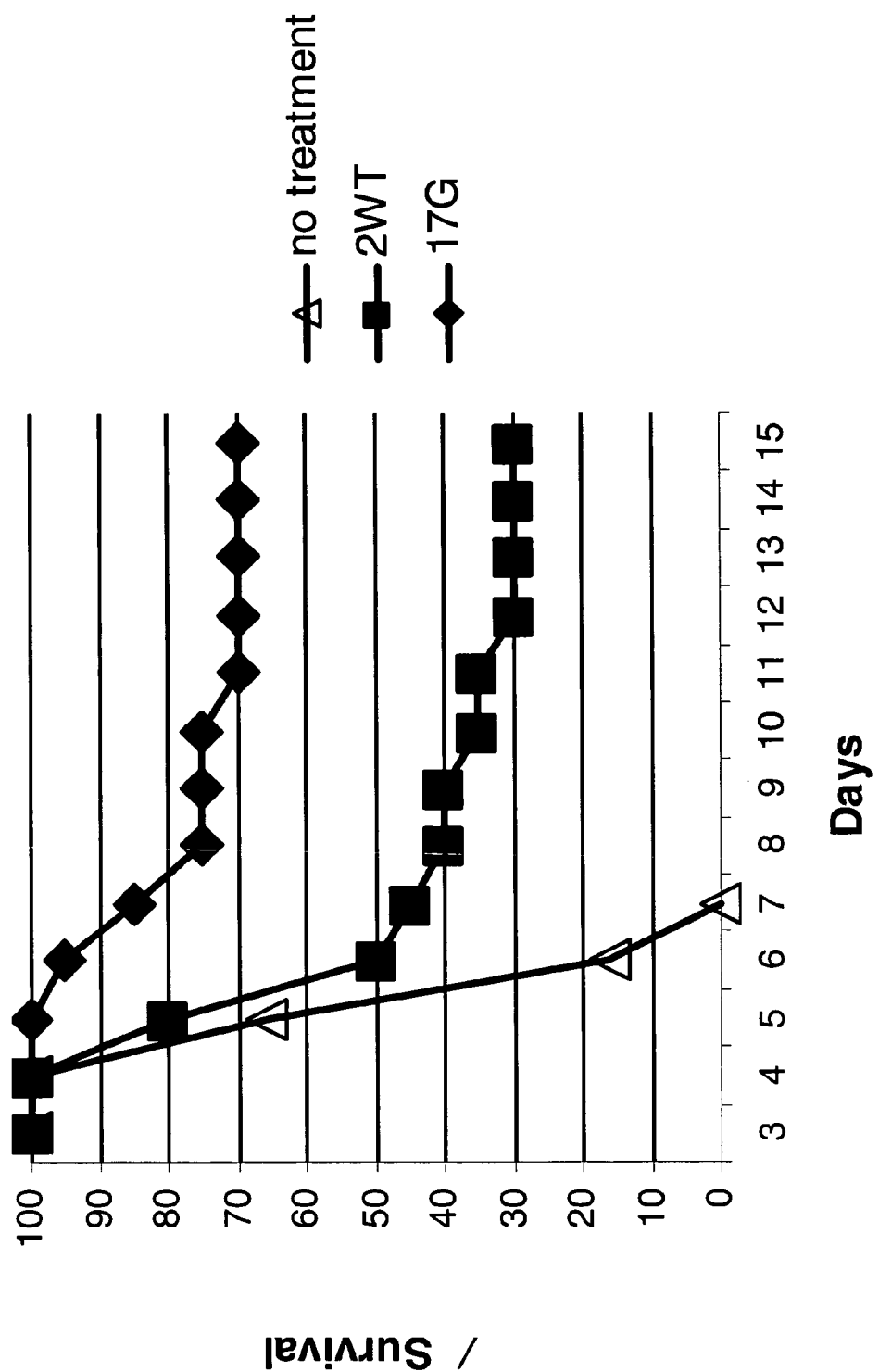
FIG. 4 represents the survival rate of mice previously infected by VSV virus and treated with G45R mutated IFNα-17 protein, in comparison to those treated with wild-type IFNα-2, or those that have not been treated.

Results are presented in FIG. 4 and indicate that the relative survival rate of the mice which have been treated with G45R mutated IFNα-17 is much higher than the survival rate of the non-treated mice, and even higher that that observed for the mice which have been treated with wild-type IFNα-2. These data demonstrate the strong antiviral activity of G45R mutated IFNα-17 in vivo in mouse model.

All of these results demonstrate that G45R mutated IFNα-17 possesses unique biological properties.

The invention claimed is:

1. An isolated polypeptide comprising:
   a) the amino acid sequence of SEQ ID NO: 2 or
   b) the amino acid sequence of amino acids 24 through 189 of SEQ ID NO: 2;
      wherein said sequence comprises a G45R SNP.

2. A composition comprising the polypeptide of claim 1 and at least one excipient.

3. The composition of claim 2, wherein said excipeint is a pharmaceutically acceptable excipient.

4. The composition of 2, wherein said excipient is a buffer, aqueous vehicle, non-aqueous vehicle, wetting agent, dispersant, emulsifier, or preservative.

5. A pharmaceutical composition comprising the polypeptide of claim 1 and a pharmaceutically acceptable excipient.

6. The pharmaceutical composition of 5, wherein said excipient is a buffer, aqueous vehicle, non-aqueous vehicle, wetting agent, dispersant, emulsifier, or preservative.

7. An isolated polypeptide comprising an amino acid sequence at least 95% identical to
   a) the amino acid sequence of SEQ ID NO: or
   b) the amino acid sequence of amino acids 24 through 189 of SEQ ID NO: 2;
      wherein said sequence comprises a G45R SNP and said polypeptide exhibits at least one antiviral activity, antiproliferative activity, or immunomodulatory activity;
      wherein said antiviral activity is against vesicular stomatitis virus or encephalomyocarditis virus;
      wherein said antiproliferative activity is against TF-1 or Daudi Burkitt's cell line;
      wherein said immunomodulatory activity is dendritic cell maturation, cytokine release by monocytes, CD4+ T-lymphocytes, or CD8+ T-lymphocytes.

8. The polypeptide of claim 7, wherein said amino acid sequence is at least 97% identical to the amino acid sequence SEQ ID NO: 2.

9. The polypeptide of claim 7, wherein said amino acid sequence is at least 99% identical to the amino acid sequence SEQ ID NO: 2.

10. The polypeptide of claim 7, wherein said amino acid sequence is at least 97% identical to the amino acid sequence of amino acids 24 through 189 of SEQ ID NO: 2.

11. The polypeptide of claim 7, wherein said amino acid sequence is at least 99% identical to the amino acid sequence of amino acids 24 through 189 of SEQ ID NO: 2.

12. A composition comprising the polypeptide of claim 7 and at least one excipient.

13. The composition of claim 12, wherein said excipeint is a pharmaceutically acceptable excipient.

14. The composition of 12, wherein said excipient is a buffer, aqueous vehicle, non-aqueous vehicle, wetting agent, dispersant, emulsifier, or preservative.

15. A pharmaceutical composition comprising the polypeptide of claim 7 and a pharmaceutically acceptable excipient.

16. The pharmaceutical composition of 15, wherein said excipient is a buffer, aqueous vehicle, non-aqueous vehicle, wetting agent, dispersant, emulsifier, or preservative.

* * * * *

SEQUENCE LISTING

<160> NUMBER OF SEQ ID NOS: 5

<210> SEQ ID NO 1
<211> LENGTH: 1873
<212> TYPE: DNA
<213> ORGANISM: Homo sapiens

<400> SEQUENCE: 1

```
agcttcatac actaagagaa aaattttaaa aaattattga ttcttatttt caggagtttt      60
gaatgatcag gtatgtaatt atattcatat tattaatgtg tatttatata gatttttatt     120
ttgcacaggt actttgatac aaaatttaca tgaacaaatt acactaaaag ttatttcaca     180
aatatactta tcaagttaag ttaaatgcaa tagctttaaa cttagatttt aatttaactt     240
tttctatcat cattctttac attaaataaa aaaagcaaac tttatagttt ttatctataa     300
agtagaggta tacatagtat acataaatac atatgccaaa tctgtgttat taaaacttca     360
tgaagatttc gattacaaaa aaataccgta aaagactttg agtgcagaag aaaaatgggc     420
aatgatgaaa aacaatgaaa aacattctta aacacatgta gagagtgcaa aaagaaagca     480
aaaacagaca tagaaagtaa aactagggca tttagaaaat ggaaattagt atgttcacta     540
tttaaggcct atgcacagag caaagtcttc agaaaaccta gaggccaaag ttcaaggtta     600
cccatctcaa gtagcctagc aacatttgca acatcccaat ggccctgtcc ttttctttac     660
tgatggccgt gctggtgctc agctacaaat ccatctgttc tctaggctgt gatctgcctc     720
agacccacag cctgggtaat aggagggcct tgatactcct ggcacaaatg ggaagaatct     780
ctcctttctc ctgcctgaag gacagacatg actttggact tccccaggag gagtttgatg     840
gcaaccagtt ccagaagact caagccatct ctgtcctcca tgagatgatc cagcagacct     900
tcaatctctt cagcacagag gactcatctg ctgcttggga acagagcctc ctagaaaaat     960
tttccactga acttaccag caactgaata acctggaagc atgtgtgata caggaggttg    1020
ggatggaaga gactcccctg atgaatgagg actccatcct ggctgtgagg aaatacttcc    1080
aaagaatcac tctttatcta acagagaaga atacagccc ttgtgcctgg gaggttgtca    1140
gagcagaaat catgagatct ctctcttttt caacaaactt gcaaaaaata ttaaggagga    1200
aggattgaaa actggttcaa catggcaatg atcctgattg actaatacat tatctcacac    1260
tttcatgagt tcctccattt caaagactca cttctataac caccacgagt tgaatcaaaa    1320
ttttcaaatg ttttcagcag tgtaaagaag cgtcgtgtat acctgtgcag gcactagtac    1380
tttacagatg accatgctga tgtctctgtt catctattta tttaaatatt tatttaatta    1440
tttttaagat ttaaattatt ttttatgta atatcatgtg tacctttaca ttgtggtgaa    1500
tgtaacaata tatgttcttc atatttagcc aatatattaa tttcctttt cattaaattt    1560 ttactataca aaatttcttg tgtttgttta ttctttaaga taaaatgtcg aggctgactt    1620
```

-continued

```
tacaacctga cttaaaaata tatgatttaa ttaagttatc tatcataatt ttattcaagt    1680
tattaaaaaa acatttttct gttactggtt atatgttgcc ttcaagatat aaacgtgaac    1740
ataaaatata cagtccctgt tctcttgtat ctttgatttt tgtcaggaaa gaaatctaaa    1800
aacaataata atgctgaatt aatatcagtg atgctaactg ctataatgtg aggaagtaaa    1860
atacaatgaa ttc                                                       1873
```

```
<210> SEQ ID NO 2
<211> LENGTH: 189
<212> TYPE: PRT
<213> ORGANISM: Homo sapiens

<400> SEQUENCE: 2
```

| Met | Ala | Leu | Ser | Phe | Ser | Leu | Leu | Met | Ala | Val | Leu | Val | Leu | Ser | Tyr |
|---|---|---|---|---|---|---|---|---|---|---|---|---|---|---|---|
| 1 |  |  |  | 5 |  |  |  |  | 10 |  |  |  |  | 15 |  |

| Lys | Ser | Ile | Cys | Ser | Leu | Gly | Cys | Asp | Leu | Pro | Gln | Thr | His | Ser | Leu |
|  |  |  | 20 |  |  |  |  | 25 |  |  |  |  | 30 |  |  |

| Gly | Asn | Arg | Arg | Ala | Leu | Ile | Leu | Leu | Ala | Gln | Met | Gly | Arg | Ile | Ser |
|  |  |  | 35 |  |  |  |  | 40 |  |  |  |  | 45 |  |  |

| Pro | Phe | Ser | Cys | Leu | Lys | Asp | Arg | His | Asp | Phe | Gly | Leu | Pro | Gln | Glu |
|  | 50 |  |  |  |  | 55 |  |  |  |  | 60 |  |  |  |  |

| Glu | Phe | Asp | Gly | Asn | Gln | Phe | Gln | Lys | Thr | Gln | Ala | Ile | Ser | Val | Leu |
| 65 |  |  |  |  | 70 |  |  |  |  | 75 |  |  |  |  | 80 |

| His | Glu | Met | Ile | Gln | Gln | Thr | Phe | Asn | Leu | Phe | Ser | Thr | Glu | Asp | Ser |
|  |  |  |  | 85 |  |  |  |  | 90 |  |  |  |  | 95 |  |

| Ser | Ala | Ala | Trp | Glu | Gln | Ser | Leu | Leu | Glu | Lys | Phe | Ser | Thr | Glu | Leu |
|  |  |  | 100 |  |  |  |  | 105 |  |  |  |  | 110 |  |  |

| Tyr | Gln | Gln | Leu | Asn | Asn | Leu | Glu | Ala | Cys | Val | Ile | Gln | Glu | Val | Gly |
|  |  |  | 115 |  |  |  |  | 120 |  |  |  |  | 125 |  |  |

| Met | Glu | Glu | Thr | Pro | Leu | Met | Asn | Glu | Asp | Ser | Ile | Leu | Ala | Val | Arg |
|  |  | 130 |  |  |  |  | 135 |  |  |  |  | 140 |  |  |  |

| Lys | Tyr | Phe | Gln | Arg | Ile | Thr | Leu | Tyr | Leu | Thr | Glu | Lys | Lys | Tyr | Ser |
| 145 |  |  |  |  | 150 |  |  |  |  | 155 |  |  |  |  | 160 |

| Pro | Cys | Ala | Trp | Glu | Val | Val | Arg | Ala | Glu | Ile | Met | Arg | Ser | Leu | Ser |
|  |  |  | 165 |  |  |  |  | 170 |  |  |  |  | 175 |  |  |

| Phe | Ser | Thr | Asn | Leu | Gln | Lys | Ile | Leu | Arg | Arg | Lys | Asp |  |  |  |
|  |  |  | 180 |  |  |  |  | 185 |  |  |  |  |  |  |  |

```
<210> SEQ ID NO 3
<211> LENGTH: 57
<212> TYPE: PRT
<213> ORGANISM: Homo sapiens

<400> SEQUENCE: 3
```

| Met | Ala | Leu | Ser | Phe | Ser | Leu | Leu | Met | Ala | Val | Leu | Val | Leu | Ser | Tyr |
|---|---|---|---|---|---|---|---|---|---|---|---|---|---|---|---|
| 1 |  |  |  | 5 |  |  |  |  | 10 |  |  |  |  | 15 |  |

| Lys | Ser | Ile | Cys | Ser | Leu | Gly | Cys | Asp | Leu | Pro | Gln | Thr | His | Ser | Leu |
|  |  |  | 20 |  |  |  |  | 25 |  |  |  |  | 30 |  |  |

| Gly | Asn | Arg | Arg | Ala | Leu | Ile | Leu | Leu | Ala | Gln | Met | Gly | Arg | Ile | Ser |
|  |  |  | 35 |  |  |  |  | 40 |  |  |  |  | 45 |  |  |

| Pro | Phe | Ser | Cys | Leu | Lys | Asp | Arg | Gln |
|  | 50 |  |  |  |  | 55 |  |  |

```
<210> SEQ ID NO 4
<211> LENGTH: 20
<212> TYPE: DNA
```

```
<213> ORGANISM: Homo sapiens

<400> SEQUENCE: 4
ttcaaggtta cccatctcaa                                                    20

<210> SEQ ID NO 5
<211> LENGTH: 21
<212> TYPE: DNA
<213> ORGANISM: Homo sapiens

<400> SEQUENCE: 5
ttagtcaatc aggatcattg c                                                  21
```